(12) United States Patent
Torney et al.

(10) Patent No.: US 10,626,406 B2
(45) Date of Patent: Apr. 21, 2020

(54) METHOD FOR PLANT IMPROVEMENT

(71) Applicant: GENOPLANTE-VALOR, Paris (FR)

(72) Inventors: François Torney, Chappes (FR);
Jérôme Martin, Chappes (FR);
Stéphane Lafarge, Chappes (FR)

(73) Assignee: GENOPLANTE-VALOR, Paris (FR)

( * ) Notice: Subject to any disclaimer, the term of this patent is extended or adjusted under 35 U.S.C. 154(b) by 34 days.

(21) Appl. No.: 15/751,192

(22) PCT Filed: Jul. 29, 2016

(86) PCT No.: PCT/EP2016/068246
§ 371 (c)(1),
(2) Date: Feb. 8, 2018

(87) PCT Pub. No.: WO2017/025360
PCT Pub. Date: Feb. 16, 2017

(65) Prior Publication Data
US 2018/0230480 A1    Aug. 16, 2018

(30) Foreign Application Priority Data
Aug. 10, 2015 (EP) ........................................ 1536282

(51) Int. Cl.
*C12N 15/82* (2006.01)
*C07K 14/415* (2006.01)
*C12Q 1/6895* (2018.01)

(52) U.S. Cl.
CPC ........ *C12N 15/8227* (2013.01); *C07K 14/415* (2013.01); *C12N 15/8261* (2013.01); *C12N 15/8271* (2013.01); *C12Q 1/6895* (2013.01); *C12Q 2600/13* (2013.01); *C12Q 2600/156* (2013.01); *Y02A 40/146* (2018.01)

(58) Field of Classification Search
None
See application file for complete search history.

(56) References Cited

U.S. PATENT DOCUMENTS

| | | | | |
|---|---|---|---|---|
| 7,427,676 | B2 * | 9/2008 | Hatzfeld | ............ C12N 15/8216 435/320.1 |
| 8,686,226 | B2 * | 4/2014 | Heard | .................. C07K 14/415 435/419 |
| 2013/0081153 | A1 * | 3/2013 | Dolan | ................ C12N 15/8261 800/278 |
| 2015/0218578 | A1 | 8/2015 | Rothstein et al. | |

FOREIGN PATENT DOCUMENTS

| WO | 2013136273 A2 | 9/2013 | | |
|---|---|---|---|---|
| WO | WO-2013136273 A2 * | 9/2013 | ............... | C12N 9/93 |

OTHER PUBLICATIONS

Zhang et al. (NCBI, GenBank Sequence Accession No. JF951944, Published Feb. 9, 2012.*
Gibbs et al. (New Phytol., 203:1194-1207; 2014).*
Yoshida et al. (Plant Physiol., 167:693-710, Mar. 2015).*
Yoon et al. (Journal of Integrative Plant Biology, 57:902-912; 2015).*
Mowla et al. (Aging Cell, 13:773-779; 2014).*
Smith et al. (Nature Biotechnology, 15:1222-1223, 1997).*
Bork et al. (TIG, 12:425-427, 1996).*
Doerks et al., (TIG, 14:248-250, 1998).*
Wells (Biochemistry 29:8509-8517, 1990).*
Guo et al. (PNAS, 101: 9205-9210, 2004 ).*
Ngo et al., (The Protein Folding Problem and Tertiary Structure Prediction, K. Merz., and S. Le Grand (eds.) pp. 492-495,1994).*
Thornton et al. (Nature structural Biology, structural genomics supplement, Nov. 2000).*
Keskin et al. (Protein Science, 13:1043-1055, 2004).*
McConnell et al. (Nature, 411:709-713, 2001).*
Hanzawa et al. (PNAS, 102:7748-7753, 2005).*
Wishart et al. (JBC, 270:26782-26785, 1995).*
Nishimura et al. (Plant Cell Physiol., 41(5):583-590, 2000).*
Yang et al. (PNAS, 98:11438-11443, 2001).*
Kim et al. (Physiologia Plantarum 139: 229-240, 2010).*
Zhang et al. (J Exp. Bot., 63:203-214, 2012).*
International Search Report and Written Opinion dated Oct. 14, 2016, in the PCT Application No. PCT/EP2016/068246.
Lea, Unni S. et al., "Nitrogen deficiency enhances expression of specific MYB and bHLH transcription factors and accumulation of end products in the flavonoid pathway," PLANTA, 2007, vol. 225, pp. 1245-1253.
Dubos, Christian et al., "MYB transcription factors in Arabidopsis," Trends in Plants Science, 2010, vol. 15, No. 10, pp. 573-581.
Nemie-Feyissa, Dugassa et al., "Nitrogen depletion and small R3-MYB transcription factors affecting anthocyanin accumulation in *Arabidopsis* leaves," Phytochemistry, 2014, vol. 98, pp. 34-40.
Zhang, Lichao et al., "Molecular characterization of 60 isolated wheat MYB genes and analysis of their expression during abiotic stress," Journal of Experimental Botany, 2011, vol. 63, No. 1, pp. 203-214.
Zhong, Ruiqin et al., "Secondary Cell Walls: Biosynthesis, Patterned Deposition and Transcriptional Regulation," Plant and Cell Physiology, 2014, vol. 56, No. 2, pp. 195-214.
He, Yanan et al., "Ectopic expression of a wheat MYB transcription factor gene, TaMYB73, improves salinity stress tolerance in *Arabidopsis thaliana*," Journal of Experimental Botany, 2011, vol. 63, No. 3, pp. 1511-1522.
Jia, Guanqing et al., "Cloning and characterization of a novel R1-MYB transcription factor in maize," Progress in Natural Science, 2009, vol. 19, pp. 1089-1096.
Rubio, Vicente et al., "A conserved MYB transcription factor involved in phosphate starvation signaling both in vascular plants and in unicellular algae," Genes and Development, Cold Spring Harbor Laboratory Press, Plainview, New York, US, 2001, vol. 15, pp. 2122-2133.

(Continued)

*Primary Examiner* — Vinod Kumar
(74) *Attorney, Agent, or Firm* — Polsinelli PC

(57) ABSTRACT

The invention relates to the field of plant improvement, in particular of the improvement of yield for plants, by using a transgene containing an root-specific promoter driving expression of a MYB-related protein.

14 Claims, 3 Drawing Sheets
Specification includes a Sequence Listing.

(56) References Cited

OTHER PUBLICATIONS

Greco, Maria et al., "In Posidonia oceanica cadmium induces changes in DNA methylation and chromatin patterning," Journal of Experimental Botany, 2011, vol. 63, No. 2, pp. 695-709.
Zhang, Lichao et al., "A wheat R2R3-MYB gene, TaMYB30-B, improves drought stress tolerance in transgenic *Arabidopsis*," Journal of Experimental Botany, 2012, vol. 63, No. 16, pp. 5873-5885.
Baranowskij, Nadja et al., "A novel DNA binding protein with homology to Myb oncoproteins containing only one repeat can function as a transcriptional activator," The ENBO Journal, vol. 13, No. 22, 1994, pp. 5383-5392.
Howe, K. M. et al., "Characterization of the sequence-specific interaction of mouse c-myb protein with DNA," The EMBO Journal, vol. 9, No. 1, 1990, pp. 161-169.
Klempnauer, Karl-Heinz et al., "The highly conserved amino-terminal region of the protein encoded by the v-myb oncogene functions as a DNA-binding domain," The EMBO Journal, vol. 6, No. 9, 1987, pp. 2719-2725.
Sakura, Hiroshi et al., "Delineation of three functional domains of the transcriptional activator encoded by the c-myb protooncogene," Proc. Natl. Acad. Sci. USA, vol. 86, 1989, pp. 5758-5762.
Zhang, Lichao et al., "Molecular characterization of 60 isolated wheat MYB genes and analysis of their expression during abiotic stress," Journal of Experimental Botany, 2011, pp. 1-12.

\* cited by examiner

| Promoter | Location type | Location | Year | Nb of Replicate | Number of events | % compare to controls | Prob.>f constrast | Phenotype |
|---|---|---|---|---|---|---|---|---|
| Constitutive | ND | 1 | 2014 | 4 | 5 | 97.3 | 1.60E-01 | Yield |
| Constitutive | ND | 2 | 2014 | 4 | 5 | 91.5 | 6.30E-07 | Yield |
| Constitutive | ND | 1 | 2014 | 4 | 5 | 92 | 5.40E-04 | Moisture |
| Constitutive | ND | 2 | 2014 | 4 | 5 | 101.2 | 2.90E-01 | Moisture |
| Root | ND | 1 | 2014 | 4 | 7 | 105.1 | 5.20E-03 | Yield |
| Root | ND | 3 | 2013 | 4 | 10 | 108 | 2.50E-02 | Yield |
| Root | ND | 2 | 2014 | 4 | 7 | 102.6 | 7.60E-02 | Yield |
| Root | ND | 2 | 2013 | 4 | 10 | 100.7 | 8.40E-01 | Yield |
| Root | Normal | 3 | 2014 | 4 | 7 | 106.5 | 2.10E-03 | Yield |
| Root | Normal | 2 | 2014 | 4 | 7 | 103.6 | 3.40E-04 | Yield |
| Root | ND | 1 | 2014 | 4 | 7 | 102.1 | 3.10E-01 | Moisture |
| Root | ND | 3 | 2013 | 4 | 10 | 101.1 | 2.40E-01 | Moisture |
| Root | ND | 2 | 2014 | 4 | 7 | 98.9 | 2.90E-01 | Moisture |
| Root | ND | 2 | 2013 | 4 | 10 | 101.1 | 2.30E-02 | Moisture |
| Root | Normal | 3 | 2014 | 4 | 7 | 99.9 | 8.00E-01 | Moisture |
| Root | Normal | 2 | 2014 | 4 | 7 | 99.6 | 6.30E-01 | Moisture |

Figure 3

| | |
|---|---|
| SEQ ID NO: 4 | ARKARRCWSPELHRLFVAALHQLGGPQVATPKQIREVMKVDGLTNDEVKSHLQYRLHNR |
| SEQ ID NO: 5 | SRKARRCWSPELHRLFVAALHELGGPQVATPKQIREVMQVDGLTNDEVKSHLQYRLHNP |
| SEQ ID NO: 6 | SRKARRCWSPELHRRFVAALHELGGPQVATPKQIREVMQVDGLTNDEVKSHLQ-YRLHNP |
| SEQ ID NO: 7 | ARKSRRCWSPELHRQFVAALQQLGGPQVATPKQIREVMQVDGLTNDEVKSHLQYRLHNR |
| SEQ ID NO: 3 | ARKTRRCWSPELHRQFVAALRQLGGPQVATPKQIREVMQVDGLTNDEVKSHLQYRLHNR |
| SEQ ID NO: 8 | SRKTRRCWSPELHRHFVAALHQLGGPQVATPKQIREVMKVDGLTNDEVKSHLQYRLHNQ |
| SEQ ID NO: 2 | SRKTRRCWSPELHRRFVAALHQLGGPQVATPKQIREVMQVDGLTNDEVKSHLQYRLHNQ |

Figure 4

SEQUENCE LISTING

```
<160> NUMBER OF SEQ ID NOS: 26

<210> SEQ ID NO 1
<211> LENGTH: 1005
<212> TYPE: DNA
<213> ORGANISM: Triticum monococcum

<400> SEQUENCE: 1
atgggcctcg acgtcggcga gatcggtatg ccgctcgatt tgggcctcga cctcaggctc      60
ttcgtggcca agacagccgg tcggcttgcg aaggaggccc cagccgtcga cgcctgcatc     120
cggggcctcg aggaggagcg ccgtaagatc gaggtctttc gcagggagct gcccttgtgc     180
gctcggcttc tcgcggacgt cattgagttc atgaaggaag aggcggcaaa gaggagtgag     240
cgtcgtgatg cggacgacaa cgacaagcgc aagtggatgt cgaccgccca attgtgggtt     300
aactcaaggg cgaccgacgc agccgaccct gtcaaggagc aaaagaagga gtccgccctc     360
tcaaagccta tgctcttggg gggcgctacc ggggtcccga tggccgttag ctgcggcgct     420
```

```
atgcccctc cagccgcacc ccactacctg ggtcgcgaag acaagatcgt cggaacggag      480 cgtctcccg cgttgccgat gatttcgccg gctgccaaca ggcagttctc tccgccagct      540
gacgataggc atcaagcctt cgccgcgaag ttcgcgtcgg ccatgccgcc cccaggccct      600
ggactgcagg cccatgagca gcaaagcagg aagactagac ggtgctggtc tcccgagttg      660
caccgccatt ttgttgcggc cctccaccag ctcggcggtc ctcaggtggc acccccaag      720 caaatcaggg aggtcatgaa ggttgacggg cttacgaacg acgaggtcaa gtcccacctc      780
cagaagtaca gacttcacaa ccaaaggtgt ccatcctcgt cgtcggcctc ccacccagtg      840
atgcttgtgg cgacctttg ggccaccaa gagcagagtt ccagccagag ccggtcccca      900
gagggcccac tgcagctctc tgtttcgggc gtcgccgtct cagcactgac cggcagcgac      960
agcagtgagg aggacgacag atccgtgggc tactcccgcc gttaa                     1005
```

<210> SEQ ID NO 2
<211> LENGTH: 334
<212> TYPE: PRT
<213> ORGANISM: Triticum monococcum

<400> SEQUENCE: 2

```
Met Gly Leu Asp Val Gly Glu Ile Gly Met Pro Leu Asp Leu Gly Leu
1               5                   10                  15

Asp Leu Arg Leu Phe Val Ala Lys Thr Ala Gly Arg Leu Ala Lys Glu
            20                  25                  30

Ala Pro Ala Val Asp Ala Cys Ile Arg Gly Leu Glu Glu Arg Arg
        35                  40                  45

Lys Ile Glu Val Phe Arg Arg Glu Leu Pro Leu Cys Ala Arg Leu Leu
    50                  55                  60

Ala Asp Val Ile Glu Phe Met Lys Glu Glu Ala Lys Arg Ser Glu
65                  70                  75                  80

Arg Arg Asp Ala Asp Asp Asn Asp Lys Arg Lys Trp Met Ser Thr Ala
                85                  90                  95

Gln Leu Trp Val Asn Ser Arg Ala Thr Asp Ala Ala Asp Pro Val Lys
            100                 105                 110

Glu Gln Lys Lys Glu Ser Ala Leu Ser Lys Pro Met Leu Leu Gly Gly
        115                 120                 125

Ala Thr Gly Val Pro Met Ala Val Ser Cys Gly Ala Met Pro Pro Pro
    130                 135                 140

Ala Ala Pro His Tyr Leu Gly Arg Glu Asp Lys Ile Val Gly Thr Glu
145                 150                 155                 160

Arg Leu Pro Ala Leu Pro Met Ile Ser Pro Ala Ala Asn Arg Gln Phe
                165                 170                 175

Ser Pro Pro Ala Asp Asp Arg His Gln Ala Phe Ala Ala Lys Phe Ala
            180                 185                 190

Ser Ala Met Pro Pro Gly Pro Gly Leu Gln Ala His Glu Gln Gln
        195                 200                 205

Ser Arg Lys Thr Arg Arg Cys Trp Ser Pro Glu Leu His Arg His Phe
    210                 215                 220

Val Ala Ala Leu His Gln Leu Gly Gly Pro Gln Val Ala Thr Pro Lys
225                 230                 235                 240

Gln Ile Arg Glu Val Met Lys Val Asp Gly Leu Thr Asn Asp Glu Val
                245                 250                 255

Lys Ser His Leu Gln Lys Tyr Arg Leu His Asn Gln Arg Cys Pro Ser
            260                 265                 270
```

```
Ser Ser Ser Ala Ser His Pro Val Met Leu Val Gly Asp Leu Trp Ala
        275                 280                 285

His Gln Glu Gln Ser Ser Gln Ser Arg Ser Pro Glu Gly Pro Leu
    290                 295                 300

Gln Leu Ser Val Ser Gly Val Ala Val Ser Ala Leu Thr Gly Ser Asp
305                 310                 315                 320

Ser Ser Glu Glu Asp Asp Arg Ser Val Gly Tyr Ser Arg Arg
                325                 330

<210> SEQ ID NO 3
<211> LENGTH: 349
<212> TYPE: PRT
<213> ORGANISM: Brachypodium distachyon

<400> SEQUENCE: 3

Met Gly Leu Asp Val Gly Glu Ile Gly Ala Pro Leu Asp Leu Gly Leu
1               5                   10                  15

Asp Leu Lys Leu Phe Val Ala Arg Thr Ala Gly Arg Leu Ala Ala Ala
            20                  25                  30

Lys Glu Ala Pro Ser Met Asp Ala Cys Ile Arg Gly Leu Glu Glu Glu
        35                  40                  45

Arg Arg Lys Ile Glu Val Phe Arg Arg Glu Leu Pro Leu Cys Val Arg
    50                  55                  60

Leu Leu Ala Glu Val Ile Glu Met Met Lys Glu Gln Ala Gly Lys Arg
65                  70                  75                  80

Ser Glu Val Arg Asp Ala Glu Ala Lys Ala Glu Asp Asn Asp Lys Arg
                85                  90                  95

Lys Trp Met Ser Thr Ala Gln Leu Trp Val Asp Asn Arg Gly Ser Asp
            100                 105                 110

Ser Asp Ser Val Val Gln Lys Glu Gln Lys Glu Thr Thr Leu Pro
        115                 120                 125

Lys Pro Met Leu Leu Gly Gly Ala Gly Gly Ala Pro Ala Pro Leu Met
    130                 135                 140

Ala Val Gly Phe Gly Ala Met Pro Pro Pro Ala Pro Pro Ser Ser Gln
145                 150                 155                 160

Tyr Phe Ser Arg Glu Asp Lys Val Ala Ala Ser Thr Glu Gly Leu Pro
                165                 170                 175

Ala Leu Pro Met Met Ser Pro Val Leu Lys Arg Pro Phe Ser Pro Gly
            180                 185                 190

Val Asp Asp Arg Arg Pro Ala Pro Ser Ala Lys Phe Ala Thr Ile Met
        195                 200                 205

Pro Pro Pro Ala Leu Ser Leu Gln Ser Gln Glu Gln Gln Ala Arg Lys
    210                 215                 220

Thr Arg Arg Cys Trp Ser Pro Glu Leu His Arg Gln Phe Val Ala Ala
225                 230                 235                 240

Leu Arg Gln Leu Gly Gly Pro Gln Val Ala Thr Pro Lys Gln Ile Arg
                245                 250                 255

Glu Val Met Lys Val Asp Gly Leu Thr Asn Asp Glu Val Lys Ser His
            260                 265                 270

Leu Gln Lys Tyr Arg Leu His Asn Gln Arg Ser Ser Gly Ser Ser Ser
        275                 280                 285

Ser Ser His Ser Ile Val Leu Val Gly Asp His Trp Pro Pro Gln Glu
    290                 295                 300

Gln Ser Ser Ser Gln Ser Arg Ser Pro Glu Ala Glu Gly Pro Leu Gln
```

```
                    305                 310                 315                 320
          Phe Ser Ser Ser Gly Val Ala Val Ser Ala Ala Thr Val Ser Asp Ser
                              325                 330                 335

Ser Glu Glu Asp Asp Arg Ser Asp Gly His Ser Arg Lys
                              340                 345

<210> SEQ ID NO 4
<211> LENGTH: 338
<212> TYPE: PRT
<213> ORGANISM: Zea mays

<400> SEQUENCE: 4

Met Gly Leu Asp Val Gly Gly Ile Gly Met Gly Leu Asp Leu Gly Leu
1               5                   10                  15

Asp Leu Gly Leu Phe Ala Ala Arg Ser Ala Gly Gly Met Ala Ala Ala
                20                  25                  30

Ala Lys Gly Ala Pro Ala Glu Ile Glu Ser Cys Ile Arg Ser Leu Glu
            35                  40                  45

Glu Glu Arg Arg Lys Ile Glu Val Phe Arg Arg Glu Leu Pro Leu Cys
        50                  55                  60

Val Arg Leu Leu Ala Asp Val Ile Asp Glu Leu Lys Asp Glu Ala Ala
65                  70                  75                  80

Lys Arg Gly Gly Asp Ala Glu Ala Lys Ala Asp Asp Gly Asp Lys Arg
                85                  90                  95

Lys Trp Met Ser Thr Ala Gln Leu Trp Leu Asp Ser Asp Ala Lys Ser
            100                 105                 110

Asp Glu Ser Asp Lys Glu Gln Leu Ser Glu Ile Thr Ser Pro Glu Pro
        115                 120                 125

Lys Leu Leu Gly Gly Ala Pro Met Pro Ile Arg Ala Val Ala Ala Val
130                 135                 140

Pro Pro Leu Pro Pro Phe Phe Arg Arg Glu Asp Ser Ser Ala Gly
145                 150                 155                 160

Ser Gly Leu Ser Leu Val Pro Pro Ala Ala Lys Pro Pro Ile Pro Pro
                165                 170                 175

Met Ser Ala Ser Asp Asn Ala Ser Gly Arg Phe Cys Ala Thr Met Pro
            180                 185                 190

Pro Ser Gly Ser Gly Ala Asn Leu His Ser Gln Ala Gln Gln Gln Ala
        195                 200                 205

Arg Lys Ala Arg Arg Cys Trp Ser Pro Glu Leu His Arg Leu Phe Val
210                 215                 220

Ala Ala Leu His Gln Leu Gly Gly Pro Gln Val Ala Thr Pro Lys Gln
225                 230                 235                 240

Ile Arg Glu Val Met Lys Val Asp Gly Leu Thr Asn Asp Glu Val Lys
                245                 250                 255

Ser His Leu Gln Lys Tyr Arg Leu His Asn Arg Arg Ser Pro Gly Val
            260                 265                 270

Val Ala Pro Val Ser Gln Ser Val Met Leu Ala Gly Gly Leu Trp Ala
        275                 280                 285

Pro Pro His Gln Glu Gln Ser Ser Gln Ser Gly Ser Pro Gln Gly
290                 295                 300

Pro Leu Gln Phe Ser Gly Ser Gly Val Ala Ala Thr Val Gly Gly Asp
305                 310                 315                 320

Ser Ser Ser Ser Asp Glu Asp Asp Lys Ser Glu Gly Tyr Ser Arg Lys
                325                 330                 335
```

Tyr Val

```
<210> SEQ ID NO 5
<211> LENGTH: 362
<212> TYPE: PRT
<213> ORGANISM: Zea mays

<400> SEQUENCE: 5
```

| | | | | | | | | | | | | | | |
|---|---|---|---|---|---|---|---|---|---|---|---|---|---|---|
| Met | Gly | Leu | Asp | Val | Gly | Glu | Ile | Gly | Met | Gly | Leu | Asp | Leu | Gly | Leu |
| 1 | | | | 5 | | | | | 10 | | | | | 15 | |
| Asp | Leu | Arg | Leu | Phe | Ala | Ala | Arg | Ser | Ala | Gly | Gly | Met | Ala | Lys | Gly |
| | | | 20 | | | | | 25 | | | | | 30 | | |
| Ala | Ala | Pro | Ala | Gly | Ile | Gln | Ser | Cys | Ile | Arg | Ser | Leu | Glu | Val | Glu |
| | | | | 35 | | | | | 40 | | | | | 45 | |
| Arg | Arg | Lys | Ile | Glu | Val | Phe | Arg | Arg | Glu | Leu | Pro | Leu | Cys | Leu | Arg |
| | 50 | | | | | 55 | | | | | 60 | | | | |
| Leu | Leu | Ala | Asp | Val | Ile | Asp | Glu | Leu | Lys | Glu | Glu | Ala | Ala | Lys | Arg |
| 65 | | | | | 70 | | | | | 75 | | | | | 80 |
| Gly | Glu | Tyr | Asp | Asp | Gly | Ala | Ala | Thr | Val | Asp | Asp | Gly | Asp | Lys | Arg |
| | | | | 85 | | | | | 90 | | | | | 95 | |
| Lys | Trp | Met | Ser | Thr | Ala | Gln | Leu | Trp | Val | Asp | Ser | Asp | Ala | Lys | Ser |
| | | | 100 | | | | | 105 | | | | | 110 | | |
| Asp | Glu | Ser | Asp | Lys | Glu | Gln | Gln | Ser | Glu | Ile | Thr | Ser | Pro | Pro | Glu |
| | | | | 115 | | | | | 120 | | | | | 125 | |
| Pro | Lys | Leu | Leu | Gly | Gly | Gly | Ala | Pro | Thr | Pro | Ile | Arg | Ala | Ala | Val |
| | 130 | | | | | 135 | | | | | 140 | | | | |
| Ser | Ala | Val | Ala | Val | Pro | Gln | Pro | Leu | Pro | Pro | Leu | Phe | Arg | Arg |
| 145 | | | | | 150 | | | | | 155 | | | | | 160 |
| Glu | Asp | Ser | Ser | Ala | Ser | Ser | Gly | Leu | Ser | Leu | Val | Ser | Leu | Ser | Pro |
| | | | | 165 | | | | | 170 | | | | | 175 | |
| Ala | Thr | Lys | Ala | Ala | Val | Pro | Ile | Ser | Pro | Pro | Val | Val | Ala | Ala | Ser |
| | | | 180 | | | | | 185 | | | | | 190 | | |
| Gly | Thr | Gly | Thr | Ala | Ser | Ala | Arg | Phe | Cys | Gly | Thr | Thr | Met | Pro | Pro |
| | | | | 195 | | | | | 200 | | | | | 205 | |
| Cys | Gly | Ser | Glu | Val | Asn | Asn | Met | His | Ser | Gln | Ala | Gln | Gln | Gln | Gln |
| | 210 | | | | | 215 | | | | | 220 | | | | |
| Gln | Ala | Ser | Arg | Lys | Ala | Arg | Arg | Cys | Trp | Ser | Pro | Glu | Leu | His | Arg |
| 225 | | | | | 230 | | | | | 235 | | | | | 240 |
| Arg | Phe | Val | Ala | Ala | Leu | His | Glu | Leu | Gly | Gly | Pro | Gln | Val | Ala | Thr |
| | | | | 245 | | | | | 250 | | | | | 255 | |
| Pro | Lys | Gln | Ile | Arg | Glu | Val | Met | Gln | Val | Asp | Gly | Leu | Thr | Asn | Asp |
| | | | 260 | | | | | 265 | | | | | 270 | | |
| Glu | Val | Lys | Ser | His | Leu | Gln | Lys | Tyr | Arg | Leu | His | Asn | Arg | Arg | Ser |
| | | | | 275 | | | | | 280 | | | | | 285 | |
| Ser | Pro | Gly | Ala | Ala | Ala | Ala | Pro | Val | Ser | Gln | Ser | Ile | Met | Leu | Val |
| | 290 | | | | | 295 | | | | | 300 | | | | |
| Asp | Gly | Val | Trp | Ala | Ala | Gln | Glu | Gln | Ser | Ser | Gly | Ser | Gln | Ser | Gly |
| 305 | | | | | 310 | | | | | 315 | | | | | 320 |
| Ser | Arg | Gln | Gly | Pro | Leu | Gln | Phe | Ser | Arg | Ala | Gly | Met | Ala | Val | Gly |
| | | | | 325 | | | | | 330 | | | | | 335 | |
| Gly | Gly | Asp | Asp | Ser | Ser | Ser | Asp | Asp | Asp | Glu | Asp | Asp | Lys |
| | | | 340 | | | | | 345 | | | | | 350 | | |
| Ser | Glu | Asp | Gly | Tyr | Ser | Leu | Lys | Cys | Val |
| | | | | 355 | | | | | 360 |

<210> SEQ ID NO 6
<211> LENGTH: 361
<212> TYPE: PRT
<213> ORGANISM: Zea mays

<400> SEQUENCE: 6

Met Gly Leu Asp Val Gly Glu Ile Gly Met Gly Leu Asp Leu Gly Leu
1               5                   10                  15

Asp Leu Arg Leu Phe Ala Ala Arg Ser Ala Gly Gly Met Ala Lys Gly
            20                  25                  30

Ala Ala Pro Ala Gly Ile Gln Ser Cys Ile Arg Ser Leu Glu Val Glu
        35                  40                  45

Arg Arg Lys Ile Glu Val Phe Arg Arg Glu Leu Pro Leu Cys Leu Arg
    50                  55                  60

Leu Leu Ala Asp Val Ile Asp Glu Leu Lys Glu Ala Ala Lys Arg
65                  70                  75                  80

Gly Glu Tyr Asp Asp Gly Ala Ala Thr Val Asp Asp Gly Asp Lys Arg
            85                  90                  95

Lys Trp Met Ser Thr Ala Gln Leu Trp Val Asp Ser Asp Ala Lys Ser
            100                 105                 110

Asp Glu Ser Asp Lys Glu Gln Ser Glu Ile Thr Ser Pro Pro Glu
            115                 120                 125

Pro Lys Leu Leu Gly Gly Gly Ala Pro Thr Pro Ile Arg Ala Ala Val
    130                 135                 140

Ser Ala Val Ala Val Pro Gln Pro Leu Pro Pro Leu Phe Arg Arg
145                 150                 155                 160

Glu Asp Ser Ser Ala Ser Ser Gly Leu Ser Leu Val Ser Leu Ser Pro
            165                 170                 175

Ala Thr Lys Ala Ala Val Pro Ile Ser Pro Val Val Ala Ala Ser
            180                 185                 190

Gly Thr Gly Thr Ala Ser Ala Arg Phe Cys Gly Thr Thr Met Pro Pro
            195                 200                 205

Cys Gly Ser Glu Val Asn Asn Met His Ser Gln Ala Gln Gln Gln Gln
    210                 215                 220

Gln Ala Ser Arg Lys Ala Arg Arg Cys Trp Ser Pro Glu Leu His Arg
225                 230                 235                 240

Arg Phe Val Ala Ala Leu His Glu Leu Gly Gly Pro Gln Val Ala Thr
            245                 250                 255

Pro Lys Gln Ile Arg Glu Val Met Gln Val Asp Gly Leu Thr Asn Asp
            260                 265                 270

Glu Val Lys Ser His Leu Gln Tyr Arg Leu His Asn Arg Arg Ser Ser
    275                 280                 285

Pro Gly Ala Ala Ala Ala Pro Val Ser Gln Ser Ile Met Leu Val Asp
    290                 295                 300

Gly Val Trp Ala Ala Gln Glu Gln Ser Ser Gly Ser Gln Ser Gly Ser
305                 310                 315                 320

Arg Gln Gly Pro Leu Gln Phe Ser Arg Ala Gly Met Ala Val Gly Gly
            325                 330                 335

Gly Asp Asp Ser Ser Ser Asp Asp Asp Glu Asp Asp Lys Ser
            340                 345                 350

Glu Asp Gly Tyr Ser Leu Lys Cys Val
    355                 360

<210> SEQ ID NO 7

<211> LENGTH: 348
<212> TYPE: PRT
<213> ORGANISM: Oryza sativa

<400> SEQUENCE: 7

| Met | Gly | Leu | Asp | Val | Gly | Glu | Ile | Gly | Met | Gly | Leu | Asp | Leu | Ser | Leu |
|-----|-----|-----|-----|-----|-----|-----|-----|-----|-----|-----|-----|-----|-----|-----|-----|
| 1 | | | | 5 | | | | | 10 | | | | | 15 | |

| Asp | Leu | Lys | Met | Phe | Ala | Ala | Arg | Ser | Ala | Val | Arg | Met | Ala | Ala | Ala |
| | | | 20 | | | | | 25 | | | | | 30 | | |

| Ala | Ala | Lys | Glu | Ala | Thr | Gly | Val | Glu | Ala | Cys | Ile | Arg | Ser | Leu | Glu |
| | | | 35 | | | | | 40 | | | | | 45 | | |

| Glu | Glu | Arg | Arg | Lys | Ile | Glu | Met | Phe | Arg | Arg | Glu | Leu | Pro | Leu | Cys |
| | 50 | | | | | 55 | | | | | 60 | | | | |

| Ala | Arg | Leu | Leu | Ala | Asp | Val | Ile | Glu | Leu | Met | Lys | Glu | Glu | Ala | Gly |
| 65 | | | | | 70 | | | | | 75 | | | | | 80 |

| Lys | Arg | Arg | Lys | Asp | Gly | Asp | Ala | Glu | Ala | Lys | Ala | Glu | Asp | Gly |
| | | | | 85 | | | | 90 | | | | | 95 | |

| Asp | Lys | Thr | Lys | Trp | Met | Ser | Thr | Ala | Gln | Leu | Trp | Val | Asp | Ser | Arg |
| | | | 100 | | | | | 105 | | | | | 110 | | |

| Gly | Ser | Asp | Ala | Asp | Ser | Glu | Asn | Asp | Arg | Arg | Ser | Gly | Ser | Thr | Ser |
| | | | 115 | | | | | 120 | | | | | 125 | | |

| Pro | Ala | Ser | Arg | Leu | Leu | Gly | Gly | Ala | Glu | Glu | Ser | Ser | Arg | Ala |
| | 130 | | | | | 135 | | | | | 140 | | | | |

| Val | Ala | Pro | Pro | Pro | Tyr | Phe | Arg | Arg | Glu | Glu | Arg | Val | Val | Leu | Arg |
| 145 | | | | | 150 | | | | | 155 | | | | | 160 |

| Pro | Ala | Met | Pro | Leu | Leu | Pro | Pro | Ala | Ser | His | Arg | Ser | Pro | Pro | Pro |
| | | | | 165 | | | | | 170 | | | | | 175 | |

| Ala | Ala | Ala | Ala | Ala | Ala | Thr | Ala | Ala | Gly | Asp | Asp | His | Arg | His | Val |
| | | | 180 | | | | | 185 | | | | | 190 | | |

| Val | Ala | Ser | Ser | Phe | Ala | Thr | Ala | Val | Pro | Ser | Pro | Val | Pro | Ala | Ala |
| | | | 195 | | | | | 200 | | | | | 205 | | |

| Leu | Ser | Leu | Gln | Ala | Gln | Ala | Gln | Gln | Gln | Gln | Gln | Ala | Arg | Lys |
| | 210 | | | | | 215 | | | | | 220 | | | | |

| Ser | Arg | Arg | Cys | Trp | Ser | Pro | Glu | Leu | His | Arg | Gln | Phe | Val | Ala | Ala |
| 225 | | | | | 230 | | | | | 235 | | | | | 240 |

| Leu | Gln | Gln | Leu | Gly | Gly | Pro | Gln | Val | Ala | Thr | Pro | Lys | Gln | Ile | Arg |
| | | | | 245 | | | | | 250 | | | | | 255 | |

| Glu | Val | Met | Lys | Val | Asp | Gly | Leu | Thr | Asn | Asp | Glu | Val | Lys | Ser | His |
| | | | 260 | | | | | 265 | | | | | 270 | | |

| Leu | Gln | Lys | Tyr | Arg | Leu | His | Asn | Arg | Lys | Ser | Pro | Gly | Thr | Ala | Ser |
| | | | 275 | | | | | 280 | | | | | 285 | | |

| Ala | Ser | His | Ser | Ile | Val | Leu | Val | Gly | Asp | Leu | Trp | Ala | Ser | Gln | Glu |
| | 290 | | | | | 295 | | | | | 300 | | | | |

| Val | Ser | Cys | Ser | Gln | Ser | Gly | Ser | Pro | Gln | Gly | Pro | Leu | Gln | Leu | Ser |
| 305 | | | | | 310 | | | | | 315 | | | | | 320 |

| Gly | Ser | Gly | Val | Ala | Val | Ser | Ala | Ala | Thr | Ala | Gly | Asp | Ser | Cys | Cys |
| | | | | 325 | | | | | 330 | | | | | 335 | |

| Glu | Asp | Asp | Lys | Ser | Glu | Gly | Tyr | Val | Arg | Lys |
| | | | 340 | | | | | 345 | | |

<210> SEQ ID NO 8
<211> LENGTH: 336
<212> TYPE: PRT
<213> ORGANISM: Triticum aestivum

<400> SEQUENCE: 8

```
Met Gly Leu Asp Val Gly Glu Ile Gly Met Pro Leu Asp Leu Gly Leu
1               5                   10                  15

Asp Leu Lys Leu Phe Val Ala Lys Thr Ala Gly Arg Leu Ala Lys Glu
            20                  25                  30

Ala Pro Ala Val Asp Ala Cys Ile Arg Gly Leu Glu Glu Arg Arg
        35                  40                  45

Lys Ile Glu Val Phe Arg Arg Glu Leu Pro Leu Cys Ala Arg Leu Leu
50                  55                  60

Ala Asp Val Ile Glu Phe Met Lys Glu Glu Ala Ala Lys Arg Ser Glu
65                  70                  75                  80

Arg Arg Asp Ala Asp Asn Asp Lys Arg Lys Trp Met Ser Thr Ala
            85                  90                  95

Gln Leu Trp Val Asp Thr Arg Ala Thr Asp Ala Ala Asp Pro Val Val
            100                 105                 110

Gln Lys Glu Gln Lys Lys Glu Ser Ser Leu Ser Lys Pro Met Leu Leu
            115                 120                 125

Gly Gly Ala Ile Gly Ala Pro Met Ala Val Ser Cys Arg Ala Met Pro
130                 135                 140

Pro Pro Ala Ala Pro Gln Tyr Phe Gly Arg Asp Asp Lys Ile Val Gly
145                 150                 155                 160

Ser Gln Gly Leu Leu Ala Leu Pro Met Ile Ser Pro Ala Ala Asn Arg
            165                 170                 175

Gln Phe Ser Pro Pro Ala Asp Asp Arg His Gln Ala Phe Ala Ala Lys
            180                 185                 190

Phe Ala Ala Pro Met Pro Pro Gly Pro Gly Leu Gln Thr His Asp
            195                 200                 205

Gln Gln Ser Arg Lys Thr Arg Arg Cys Trp Ser Pro Glu Leu His Arg
210                 215                 220

His Phe Val Ala Ala Leu His Gln Leu Gly Gly Pro Gln Val Ala Thr
225                 230                 235                 240

Pro Lys Gln Ile Arg Glu Val Met Lys Val Asp Gly Leu Thr Asn Asp
            245                 250                 255

Glu Val Lys Ser His Leu Gln Lys Tyr Arg Leu His Asn Gln Arg Ser
            260                 265                 270

Pro Ser Ser Ser Ala Ser His Pro Ile Met Leu Val Gly Asp Leu
            275                 280                 285

Trp Ala His Gln Glu Gln Ser Ser Ser Gln Ser Arg Ser Pro Glu Gly
            290                 295                 300

Pro Leu Gln Leu Ser Val Ser Gly Val Ala Val Ser Ala Leu Thr Val
305                 310                 315                 320

Ser Asp Ser Ser Glu Glu Asp Asp Arg Ser Val Gly Tyr Ser Arg Arg
            325                 330                 335
```

<210> SEQ ID NO 9
<211> LENGTH: 1001
<212> TYPE: DNA
<213> ORGANISM: Hordeum vulgare

<400> SEQUENCE: 9 aacatttta atgtgttttt gtatagtgtc ttaaaaaata cttgttttgt ttaatattca      60
atagtaaaaa ggaacacaaa taataaaaag aaaaacatga aaaagaaat acaataaaac     120 aggcttgtga ttccctcccg cgtgggacgg cggttcctac gaggaggtgt tgggcaccc    180 cgggcaatcg gaggtattct cttcgtcacg gtttaaaagg catgcttgga aattatctag   240

```
aacctagatg gttattgatt agttatgaga tggactaaaa aatagcagtc acactacgca      300
tacatataga agtagtataa cagagtacta taattagctg ctatgagtaa tgaaatgcac      360
cctaaataat cttgtctatc atggaaatgc acgtaaattt aaccgtgtct tctaaatagt      420
gacggaagga gcaccaaata cattgcagtg gagtctcggg ccagttaact ttgaccctca      480
ttgataaaaa tgaataaata acttggacta tgactagcaa aactagccgg acaatttgac      540
ctaaacaggc tagctaggac ccaattacaa agcaacatg gactaacttg gactccacac      600
ctacccgaag tagcacatgg aaaggattaa ccgactcatt ctggactttt ataatctaat      660
aatcaaccga gaggccatgc atccgtctag tatataacag tatatataat aacaatccat      720
actagacgac gaggacgatt tgaacggcaa gtttcacgct gtcactccca ctctcgctct      780
cattttatta atcactaaca aacgcatgat ttgatcagac acccaaaata ggaataggag      840
atgctatcat caagcatgct tcttgctgcc cagagcatcc cacgactaca aaacacggct      900
ggccggagga ttataacacg atcgagcgac caatccaagc acctacgcac tcttctttgc      960
tctcatcctc tagctagcta actagctctc ttggatcatc c                        1001
```

```
<210> SEQ ID NO 10
<211> LENGTH: 1004
<212> TYPE: DNA
<213> ORGANISM: Oryza sativa

<400> SEQUENCE: 10
```

```
aatttgcacg gtgctagcta gctagatttt gaaagtagat gaaccgatat ataacacttt       60
gggtttcata ctttcattag tccacatgaa catcgaaccc tagcttagac acggcataaa      120
tcgatcgagg catggacgca tgtatcagta tttgcatgat tgctcgatcg agattatatt      180
accctcttac acatgcatgc atgggggaat aattcaacaa cgtctgaatg tctgattcct      240
catggaaaat tccttgtcac atctctttct ctgagtactc taacgaacaa ctggccatgt      300
atgcacatgc accccagaga caacctagct acgtaccctg catctgacac ccccacatgc      360
acgtaccatt gcatctgctt acttcggatt gataatactt acagtgaaca acacggtctc      420
ttaaaaaata gctttgatta ctatttctat tataatatat atagaaatat taacaaatat      480
ataattttat tagatcttaa caagcatttc tccatattca tccctgaaag ttggttttta      540
taggacgaga ggagtacata tttttttaaga aaattatttt ataaattatt tataatcaaa      600
tattttaaaa ttcgatctta attttgtccg aaacaacgag tattataaga gcttatttgg      660
tagagctcca actcctaaat ttagcttcaa gagttagatc tgaagtagag ttatatgaag      720
ctgcttaaac ccaactttgc atgtctagtt cattttggag atagctctac acagctcagc      780
tgaaattgtt tggtgaagct agagctgtgc caaacagggc ctccgtctgg agagaaagta      840
gcaacgcatc catgcaaacc actcttgcta taggctcgat cggctataaa tacaagacgc      900
catgacaccc caagcaaacc aacccaaagc aacacaagcc atagcagcag agccgagtag      960
ctgagctcac tgttcgatcg atcactagct cgctagctgc atcc                     1004
```

```
<210> SEQ ID NO 11
<211> LENGTH: 1010
<212> TYPE: DNA
<213> ORGANISM: Zea mays

<400> SEQUENCE: 11
```

```
tcatcgtcgt ttgtgcaatg aagccactgc ttctcatgag agcactgtca tcaccttgca       60
```

| | |
|---|---|
| actggcagtt ttcaattgct gtaccagcgc aagatccaca tattaatctt gtacgcctca | 120 |
| cctgccccaa atggaggatg ttcactggat tgctgtccca atccaaccat ctccttatcc | 180 |
| gctttatatc acagctttaa catgaatgat aaatatcgct gaacacaaga ggtgttgcaa | 240 |
| ttttaatcta ggcgacaact tactcggtca aattctcagg ccgaggtccg aggaatttct | 300 |
| cttttgttgc aggagaacca aagtcccatg aatgaactat gaagcagcag ctcggtaatg | 360 |
| gataatgatc caccgactac gctgcttcca gcagcatagt acagcacgta ctagcttgtt | 420 |
| tttcctcagt ttggttcaaa cgtccgtatt actatagtcg tgttactata gttgtgtatg | 480 |
| tgcataattg ttttatttc atttttttac cgcctaaaaa atttcctggc aaacaaagct | 540 |
| cttgtcaccc ctcctaaaaa aatagatcag tagatacacg gtagaaataa aggatcaatt | 600 |
| cacatatcac accgcgccgc cattgatttg tttaggcaag agatatcact gtatgctcca | 660 |
| aggtcttgtt cctcctcgct gtctcatggc gtatcctaac gtgcgtgtct cgacctgaag | 720 |
| aaccacaact acacatcaat tcagcgagtt agggcggttg gtcgaccagt gtcagccaca | 780 |
| aaacgcggcc aaaatttaaa ttatcaatca tgtggtgatc attgcgcacc gcccatagta | 840 |
| ttgtaaggca catccgaggc aaggcagcgc attatgacgt gtatttaagg agactaagct | 900 |
| gaaggaactc tcgcatcagc ggcctgataa gctatagcca tcttcttctc tgaattccag | 960 |
| tccaagggcc ggaataccgt cagagggagt gggagagggg gggaaaaaag | 1010 |

<210> SEQ ID NO 12
<211> LENGTH: 993
<212> TYPE: DNA
<213> ORGANISM: Oryza sativa

<400> SEQUENCE: 12

| | |
|---|---|
| aacatgtgct aaaaagccaa cggtgtcaaa tattttgaaa cggagggagt attgcagcta | 60 |
| gctcgcgatt aaccaaggta gctatggccg gccgacgctt ctaactggcg cgcgtgccaa | 120 |
| ctctcgatcg actgctaatc atgcttgctt aatttggaag gccacgacaa tccattttaa | 180 |
| gtcgtataat taacctttg taattttgag tgagaccaca agtagatcga cggagacatt | 240 |
| ctacttggca tgcatgcaat gcagaaacgc gcagagctag cattatgtat gcttgtgaat | 300 |
| tgtgtgagag agaattagct agattgataa tgtacatata tgaatttgta tgcgatatat | 360 |
| atgctagtat atataatatg cagttaagtg tacaaattaa atgcactaat ttgcattaca | 420 |
| aaattaatta atacacatgt ggttattaat ttgtcccgaa gcgagaataa taaagccggg | 480 |
| ttgcagtgtg acgagagggg atgatcgatt agtttacatt acccttttga tctcatggct | 540 |
| ttgactctta gggtttgtac gctacctagc tagctttgct ttcggacaga gctagaggtg | 600 |
| attattactc cctccgtttc aaaatgtttg acaccgttga cttttagta cgtgtttgac | 660 |
| cattcgtctt attcaaaaaa tttaagtaat tatttattct tttcatatca tttgattcat | 720 |
| tgttaaataa acttcatgt acacatatag ttttacatat ttcacaattt tttttaaata | 780 |
| agacaaatgg tcaaacatgt gctaaaaagt caacggtatc aaacattttt aaacggaggg | 840 |
| agtagtaatt agaaatgaat aaaaacccta gctagctagc tacatgttga tgcgtattag | 900 |
| ttattcatga catcagctag ctaggcagac gagagtacgt cgagtagtat ttatagccgg | 960 |
| catggaggaa gcgagaggaa gcatcagcag cgc | 993 |

<210> SEQ ID NO 13
<211> LENGTH: 1264
<212> TYPE: DNA
<213> ORGANISM: Oryza sativa

<400> SEQUENCE: 13

```
tcgacgctac tcaagtggtg ggaggccacc gcatgttcca acgaagcgcc aaagaaagcc      60
ttgcagactc taatgctatt agtcgcctag gatatttgga atgaaaggaa ccgcagagtt     120
tttcagcacc aagagcttcc ggtggctagt ctgatagcca aaattaagga ggatgccaaa     180
acatgggtct tggcgggcgc gaaacacctt gataggtggc ttaccttttta acatgttcgg    240
gccaaaggcc ttgagacggt aaagttttct atttgcgctt gcgcatgtac aattttattc     300
ctctattcaa tgaaattggt ggctcactgg ttcattaaaa aaaaagaat ctagcctgtt      360
cgggaagaag aggattttgt tcgtgagaga gagagagaga gagagagaga gagagagaga     420
gaaggaggag gaggattttc aggcttcgca ttgcccaacc tctgcttctg ttggcccaag     480
aagaatccca ggcgcccatg ggctggcagt ttaccacgga cctacctagc ctaccttagc    540
tatctaagcg ggccgaccta gtagccacgt gcctagtgta gattaaagtt gccgggccag     600
caggaagcca cgctgcaatg gcatcttccc ctgtccttcg cgtacgtgaa aacaaaccca    660
ggtaagctta gaatcttctt gcccgttgga ctgggacacc caccaatccc accatgcccc    720
gatattcctc cggtctcggt tcatgtgatg tcctctcttg tgtgatcacg gagcaagcat    780
tcttaaacgg caaaagaaaa tcaccaactt gctcacgcag tcacgctgca ccgcgcgaag    840
cgacgcccga taggccaaga tcgcgagata aaataacaac caatgatcat aaggaaacaa    900
gcccgcgatg tgtcgtgtgc agcaatcttg gtcatttgcg ggatcgagtg cttcacagct    960
aaccaaatat tcggccgatg atttaacaca ttatcagcgt agatgtacgt acgatttgtt   1020
aattaatcta cgagccttgc tagggcaggt gttctgccag ccaatccaga tcgccctcgt   1080
atgcacgctc acatgatggc agggcagggt tcacatgagc tctaacggtc gattaattaa   1140
tcccggggct cgactataaa tacctcccta atcccatgat caaaaccatc tcaagcagcc   1200
taatcatctc cagctgatca agagctctta attagctagc tagtgattag ctgcgcttgt   1260
gatc                                                                1264
```

<210> SEQ ID NO 14
<211> LENGTH: 1028
<212> TYPE: DNA
<213> ORGANISM: Zea mays

<400> SEQUENCE: 14

```
gtatgcttgc tgccttgctc tcctgttcat ctccgtgcta aacctctgtc ctctgggtgg      60
gtttttgctg ggattttgag ctaatctgct ggtcccggta gaaaagatca tgtccctga     120
cgagctcaag cgctcgcctt agccgcgtcc ttgcccccccg ccatttttg cggtttcggt    180
gtgttcccgt gactcgccgg gtgcgtcatc gcctgaatct tgtctgggct ctgctgacat    240
gttcttggct agttgggttt atagattcct ctgatctaaa ccgtgcctgt gctgcgcaca    300
gaactctccc ctgtccttc ctggggtttt ggttacgtgg tggtagtaag cttggatttg    360
cacatggata aagttgttct aagctccgtg ggttgcttga gatcttgctg ttattgcgtg    420
ccgtgctcac ttttttttgca atccgaggaa tgaatttgtc gtttactcgt tttggtggat    480
tattagcgcg aaaaaaaaac tcttttttt ttttgttctt ttactacgaa aagcatcttc     540
ttggattttg ctatcttctt ttactacgaa aaactcttga gtctaggaat ttgaatttgt    600
gatgtccatt cttgcagtgc gctgtgcttt attgggaagc caaatcctat tattttctgc    660
ctctagggtc tgaatggaat cagtactctt gagacagaaa atcaatccaa tcaagttgat    720
```

```
ttctttcttt aaaaatatta tcacagaact aagtgcttgt gcggaatcag tactggcttt        780
tgtttggtgg aggatcaata cttgcttttg tttgggggtg gcaactgttt tgctataaga        840
ttccatgtgt tcctgttgag atgaatcata tatagtatag ctgcatacta caaatctgtt        900
tttcaaattt aggttgcttt ggcatgatct attttttgt cagacagact ttctaagtgg         960
tagctcttga tttcttgttc ttgtacaact ggtgctgctg aatcttgacc gtatagctcg       1020
aattgcag                                                                1028

<210> SEQ ID NO 15
<211> LENGTH: 509
<212> TYPE: DNA
<213> ORGANISM: Arabidopsis thaliana

<400> SEQUENCE: 15
ctaaatgctc ttaactgagc taattatgta atgcacatac acatatttac atagatatgc         60
atatttatat atagcatgta tattgtacta catgcattgc ttcttaatac atgtagtaaa        120
gatatatgca aaaatagtcg aaagatttgt ttacatataa atcaccaat atttattgtt         180 attgtatttt catgaataaa gtaataagat tatttgtcta atattttgat ttactagtac        240
tagaaatgaa aaggaatatg cacaatttca gcattatagt ttggtaggca aaatggagtg        300
agaatagagt ttcatagtat atactaaggt tcttaattgt gcaaatagtt gatacaagtc        360
acatgggcca agtttgtaaa tcttaaatcg aaatatgcct tcttcttttt ttgcatgaaa        420
atgctagtaa tttataagtg tgttttcaa taagagatgc taaataccaa aattaaccta        480
gttttcagtg agcgcttgca ttattgtgg                                         509

<210> SEQ ID NO 16
<211> LENGTH: 833
<212> TYPE: DNA
<213> ORGANISM: Oryza sativa

<400> SEQUENCE: 16
tcgaggtcat tcatatgctt gagaagagag tcgggatagt ccaaaataaa acaaaggtaa         60
gattacctgg tcaaaagtga aaacatcagt taaaggtgg tataagtaaa atatcggtaa        120 taaaggtgg cccaaagtga aatttactct tttctactat tataaaaatt gaggatgttt        180
tgtcggtact tgatacgtc attttttgtat gaattggttt ttaagtttat tcgcgatttg        240
gaaatgcata tctgtatttg agtcggtttt taagttcgtt gcttttgtaa atacagaggg        300
atttgtataa gaaatatctt taaaaaaccc atatgctaat ttgacataat ttttgagaaa        360
aatatatatt caggcgaatt ccacaatgaa caataataag attaaaatag cttgcccccg        420
ttgcagcgat gggtatttt tctagtaaaa taaaagataa acttagactc aaaacattta        480
caaaaacaac ccctaaagtc ctaaagccca aagtgctatg cacgatccat agcaagccca        540
gcccaaccca acccaaccca acccaccca gtgcagccaa ctggcaaata gtctccaccc        600
ccggcactat caccgtgagt tgtccgcacc accgcacgtc tcgcagccaa aaaaaaaaa        660 agaaagaaaa aaaagaaaaa gaaaacagc aggtgggtcc gggtcgtggg ggccggaaaa        720
gcgaggagga tcgcgagcag cgacgaggcc cggccctccc tccgcttcca agaaacgcc        780 ccccatcgcc actatataca tacccccccc tctcctccca tccccccaac cct              833

<210> SEQ ID NO 17
<211> LENGTH: 462
<212> TYPE: DNA
<213> ORGANISM: Oryza sativa
```

<400> SEQUENCE: 17

```
gtaaccaccc cgcccctctc ctctttcttt ctccgttttt tttttccgtc tcggtctcga      60
tctttggcct tggtagtttg ggtgggcgag aggcggcttc gtgcgcgccc agatcggtgc     120
gcgggagggg cgggatctcg cggctggggc tctcgccggc gtggatccgg cccggatctc     180
gcggggaatg gggctctcgg atgtagatct gcgatccgcc gttgttgggg gagatgatgg     240
ggggtttaaa atttccgcca tgctaaacaa gatcaggaag aggggaaaag ggcactatgg     300
tttatatttt tatatatttc tgctgcttcg tcaggcttag atgtgctaga tctttctttc     360
ttcttttttgt gggtagaatt tgaatccctc agcattgttc atcggtagtt tttcttttca     420
tgatttgtga caaatgcagc ctcgtgcgga gcttttttgt ag                        462
```

<210> SEQ ID NO 18
<211> LENGTH: 255
<212> TYPE: DNA
<213> ORGANISM: Arabidopsis thaliana

<400> SEQUENCE: 18

```
gaatttcccc gatcgttcaa acatttggga ataaagtttc ttaagattga atcctgttgc      60
cggtcttgcg atgattatca tataatttct gttgaattac gttaagcatg taataattaa     120
catgtaatgc atgacgttat ttatgagatg ggttttatg attagagtcc cgcaattata      180
catttaatac gcgatagaaa acaaaatata gcgcgcaaac taggataaat tatcgcgcgc     240
ggtgtcatct atgtt                                                     255
```

<210> SEQ ID NO 19
<211> LENGTH: 2991
<212> TYPE: DNA
<213> ORGANISM: Avena strigosa

<400> SEQUENCE: 19

```
tatgtcccta tctatatttg agtttatata gatatatctt attttctgc aaattttgat      60
atattatatg tattttttctg aatttaaata atttagttat gattttttcta agattaatgt    120
ggcaaaaaaa agaaaaatag ctaagccgtc ggcgtaggtc tgaaacctac gcgtagactt     180
gacgccgttg ctctaccgtt agcccaatgg gctacgccga cggtcatgtt tacgccgacg     240
gcggccgtcg gcctatttat tctacgccga cggcaaaatt gggccgacgc cccgtcaagc     300
tacgccgacg gtcccgacat tttgccgtcg gcgtataaaa agaccgtcgg cctatttagt     360
tattcccgta gtgtgtcggt gttgacacta ttatggtaac tatcctaacc ggtaggttac     420
aattatcagg gctttgtcat gcacatttat aaatgtgaat caggttgaac tttatttggt     480
gttcccaatc agacgttagt aaacacaata tcagattaac ctgggaaatc ttcatgtaac     540
ttagactaat aaaatgcatc tgttaccgtg tacaaatact atcactaacc agatccctgc     600
aagacaagat ccacggatca tggtgcagcg atttacgaga taatctattg actaattata     660
cttgttctag tactatctac tgacccttct ctggaagaca accatcgtgt attctgcacc     720
gatggaagtg aatagatctt tcttgtatta tccctcatga aggcactcag agcaaacttg     780
agcgaacctt ccgcattcat ttcttcacat gcggtgtctg atcagtcaaa caacctccag     840
agatttagta aaaacaatgt ctcgggattc cgcgattaat ttagtcgtct tatggcctcg     900
agtacttgtt ataataagat gatttgatac ttgcagtatc tttacaaact gctagctaaa     960
ttggacagta gctagttttg tcagtctagt acgtactaca tagtattttt ttctgtatct    1020
```

| | |
|---|---|
| agtggcacta ctgaaatctc actttccacg atttcaaata aaaattacct gatctgacat | 1080 |
| gatcactggc tacgccgaga ttctacaaat atttctataa gtagtttgtg gattccaata | 1140 |
| tatatacgga ttccgtaaag ctctcttacc gatggtatga ctttagtagt aacaaaatca | 1200 |
| taggcttcga gtgaagattg gctaccaact gtaatgtaag attgttgtcc aagataagat | 1260 |
| actcaagtta cagatgcact actctaatac taagagttat tgatctatat tacggctccc | 1320 |
| gtaccgtaga gatattgatt ctacgttcac cttcttaaaa ggagattctt gtacaatcaa | 1380 |
| aacaaatggg tctagctacc ttggtcaata tgtatttcta tcggtattta gttataaagg | 1440 |
| agaggaatac agaataattt ttttaactcc atagtacctc tattgctttc agtataaaga | 1500 |
| gtttgatgca cggttctctg tactaataaa tgttctattg ttgattgatt cttaaccgca | 1560 |
| tcctatgcaa ttttaacctc aaaaaagttt cacggtacac cgacttgcct tactagccct | 1620 |
| actgttttct tgagaaggat gttcaaactt tgggcttttg catctaaaat aagacacaca | 1680 |
| tcattttgg tttattattc aacaatgtgt gggaaaagca tacaacaatc aactcgatat | 1740 |
| accaccttcg cggagggcct cctctttaaa tgtctgggag tactacacat atgtaaagat | 1800 |
| gatgcccact tacaaagaac gaggacacca cttaaaccgg gtgtacaaag tactacacat | 1860 |
| atgtaaagat gaggccatag aacaagcaag agcaccaaga tatttagatc cactaaaatg | 1920 |
| caaccacctc gatgtccata aaaaatgatg gtgacgtaca acactcaaca aatatcgata | 1980 |
| aaaatgatag tgtcctagtt gcacatcttc taacatgttg gtgtctatta tgcacaagtg | 2040 |
| ggcatggaag caagtaaata ttgtgtacta tagctactgg tgactcgagt gtatctccaa | 2100 |
| gactcgatag caaacccgaa gcctcttcag cttgtccaca tatcattgtg gaatgttcac | 2160 |
| tacgactcgc cacgccaagc ataacctgga taagccacgt gggatatgag atttcccgca | 2220 |
| gcttccctct gagtgaggag gcagaactat acgcctcaac acgacgagcc accccctaag | 2280 |
| gctagtcata gtgggagtaa cttgggtagt aacatattcc tacatatatt gcgaactaag | 2340 |
| catttagatg acatgacatg caattaaatg atgagagaga gtcttatgat aactagctat | 2400 |
| gttaccataa catcacacat ttctaaaaaa ataaatctat attataataa ataaggtttt | 2460 |
| gcatgatacc acatctatgt tattttgcac tatgaagata gtaacttaga ctagtaacat | 2520 |
| atacatgtta ctactctaag ttactcccca caatgaccag cctaacacct tttgtactgt | 2580 |
| tttgcacatt tgcagtttac ttttttcttag gtgaagagaa aacacaagac ataatttaa | 2640 |
| tatttcaact tcattacgtg ctggtgcaaa taattttac ggtgcaattt tcgacatgat | 2700 |
| ttattgtata tttacagaaa tttatgctcc aaatttgttt ggtaccttca gtattagttt | 2760 |
| ctggacattg tacatattat gttgccgtat aagctgagct agaaggatca ttagtgtaat | 2820 |
| tccatatata tctaaatgta cctgtggaat cacatttgag gaagttccaa tgatgccctt | 2880 |
| tttgccctgc acacgcatat ataagaaccc tttgcccgca gcatagagct agtactagct | 2940 |
| agtatcccat tgcttgtttt cctcgcatac actgcccgtt gttggtgcgc a | 2991 |

<210> SEQ ID NO 20
<211> LENGTH: 6382
<212> TYPE: DNA
<213> ORGANISM: Artificial
<220> FEATURE:
<223> OTHER INFORMATION: proZmTIP2_3::TmMYB::terAtSac66

<400> SEQUENCE: 20

| | |
|---|---|
| aattacaacg gtatatatcc tgccaggaga tctctaatta attagtctag aggatcatcg | 60 |
| tcgtttgtgc aatgaagcca ctgcttctca tgagagcact gtcatcacct tgcaactggc | 120 |

-continued

```
agttttcaat tgctgtacca gcgcaagatc cacatattaa tcttgtacgc ctcacctgcc      180
ccaaatggag gatgttcact ggattgctgt cccaatccaa ccatctcctt atccgcttta      240
tatcacagct ttaacatgaa tgataaatat cgctgaacac aagaggtgtt gcaattttaa      300
tctaggcgac aacttactcg gtcaaattct caggccgagg tccgaggaat ttctcttttg      360
ttgcaggaga accaaagtcc catgaatgaa ctatgaagca gcagctcggt aatggataat      420
gatccaccga ctacgctgct tccagcagca tagtacagca cgtactagct tgttttttcct    480 cagtttggtt caaacgtccg tattactata gtcgtgttac tatagttgtg tatgtgcata      540
attgttttat tttcattttt ttaccgccta aaaaatttcc tggcaaacaa agctcttgtc      600 accccctccta aaaaaataga tcagtagata cacggtagaa ataaaggatc aattcacata    660
tcacaccgcg ccgccattga tttgtttagg caagagatat cactgtatgc tccaaggtct     720
tgttcctcct cgctgtctca tggcgtatcc taacgtgcgt gtctcgacct gaagaaccac     780
aactacacat caattcagcg agttagggcg gttggtcgac cagtgtcagc cacaaaacgc     840
ggccaaaatt taaattatca atcatgtggt gatcattgcg caccgcccat agtattgtaa     900
ggcacatccg aggcaaggca gcgcattatg acgtgtattt aaggagacta agctgaagga     960
actctcgcat cagcggcctg ataagctata gccatcttct tctctgaatt ccagtccaag    1020
ggccggaata ccgtcagagg gagtgggaga gggggggaaa aaagtctcca ccatggggct    1080
cgacgtcggc gagatcggga tgccactgga tctgggcctc gacctgcgcc tcttcgttgc    1140
gaagacggct gggaggctcg ctaaggaagc cccagctgtt gatgcgtgca tcagaggcct    1200
ggaggaagag agacgcaaga tcgaggtgtt ccgcagagag ctcccgctgt gcgcgaggct    1260
cctcgcggac gtgatcgagt tcatgaagga agaggccgcg aagaggagcg agcgcagaga    1320
tgctgatgac aacgacaagc ggaagtggat gtcgaccgcg caactgtggg tgaactccag    1380
ggcgacggac gctgccgatc cagtcaagga gcaaaagaag gagagcgctc tctccaagcc    1440
aatgctcctg ggcggggcta ccggcgtgcc gatggccgtt tcttgcggcg ctatgccccc    1500
accagctgcg ccacactacc tcggcagaga ggataagatc gtcggacgg agagactgcc     1560 agctctccca atgatctcac ccgccgccaa caggcagttc tcaccaccgg ccgacgacag    1620
gcatcaagct ttcgcggcca agttcgcctc ggccatgcca ccccaggcc cggggctcca    1680 agcccatgag cagcaaagca ggaagaccag aaggtgctgg tccccagagc tccatcgcca    1740
cttcgttgcc gcgctccacc agctcggggg cccacaggtg gctaccccaa agcaaatcag    1800
ggaggtcatg aaggttgacg gcctgaccaa cgatgaggtc aagtcccacc tccagaagta    1860
cagactccac aaccagaggt gcccgtcctc ttcgtccgct tcgcatcccg ttatgctcgt    1920
gggcgaccct tgggctcacc aagagcaatc cagctcgcaa tcaaggtccc ctgagggccc    1980
cctgcaactg agcgtgtccg gcgtggctgt ctcagccctc acggggtccg actcgtccga    2040
ggaagacgac agaagcgtgg ggtactccag gcggtgaaac ctaaatgctc ttaactgagc    2100
taattatgta atgcacatac acatatttac atagatatgc atatttatat atagcatgta    2160
tattgtacta catgcattgc ttcttaatac atgtagtaaa gatatatgca aaaatagtcg    2220
aaagatttgt ttacatataa aatcaccaat atttattgtt attgtatttt catgaataaa    2280
gtaataagat tatttgtcta atattttgat ttactagtac tagaaatgaa aaggaatatg    2340
cacaatttca gcattatagt ttggtaggca aaatggagtg agaatagagt ttcatagtat    2400
atactaaggt tcttaattgt gcaaatagtt gatacaagtc acatgggcca agtttgtaaa    2460
```

```
tcttaaatcg aaatatgcct tcttcttttt ttgcatgaaa atgctagtaa tttataagtg    2520
tgttttcaa taagagatgc taaataccaa aattaaccta gttttcagtg agcgcttgca    2580
ttattgtggg tggttgtacc tagggtttaa accagggatg aaagtaggat gggaaaatcc    2640
cgtaccgacc gttatcgtat aaccgatttt gttagtttta tcccgatcga tttcgaaccc    2700
gaggtaaaaa acgaaaacgg aacggaaacg ggatatacaa acggtaaacg gaaacggaaa    2760
cggtagagct agtttcccga ccgtttcacc gggatcccgt ttttaatcgg gatgatcccg    2820
tttcgttacc gtattttcta attcgggatg actgcaatat ggccagctcc aacacccatc    2880
cataaccact gaggcccagc ccatgtaaga aatacctagc gaacgctgct ctgcctctct    2940
cccaggcggc caggcaccac acgagtaaca gcatcacaca ttcacacgcc gccacgcgcc    3000
cacgccggag tccggagcta gctaattgtt attatcaata aaagaatttt tattgttatt    3060
gtgttatttg gtaatttatg cttataagta attctatgat taattgtgaa ttaataagac    3120
taatgaggat aataattgaa tttgattaaa ttaactctgc gaagccatat gtctttcacg    3180
tgagagtcac gtgatgtctc cgcgacaggc tggcacgggg cttagtatta cccccgtgcc    3240
gggatcagag acatttgact aaatgttgac ttggaataat agcccttgga ttagatgaca    3300
cgtggacgct caggatctgt gatgctagtg aagcgcttaa gctgaacgaa tctgacggaa    3360
gtgcggacaa acgcacatgg actatggccc actgctttat taaagaagtg aatgacagct    3420
gtctttgctt caagacgaag taagaatag tggaaaacgc gtaaagaata agcgtactca    3480
gtacgcttcg tggctttata aatagtgctt cgtcttattc ttcgttgtat catcaacgaa    3540
gaagttaagc tgatgcggcc gcgaattccc cgggccaggt ccgtcgcttc tcttccattt    3600
cttctcattt tcgattttga ttcttatttc tttccagtag ctcctgctct gtgaatttct    3660
ccgctcacga tagatctgct tatactcctt acattcaacc ttagatctgg tctcgattct    3720
ctgtttctct gttttttttct tttggtcgag aatctgatgt tgtttatgt tctgtcacca    3780
ttaataataa tgaactctct cattcataca atgattagtt tctctcgtct acaaaacgat    3840
atgttgcatt ttcactttc ttctttttt ctaagatgat ttgctttgac caatttgttt    3900
agatctttat tttatttat tttctggtgg gttggtggaa attgaaaaaa aaaaaaaaca    3960
gcataaattg ttatttgtta atgtattcat tttttggcta tttgttctgg gtaaaaatct    4020
gcttctacta ttgaatcttt cctggatttt ttactcctat tgggttttta tagtaaaaat    4080
acataataaa aggaaaacaa aagtttata gattctctta aaccccttac gataaaagtt    4140
ggaatcaaaa taattcagga tcagatgctc tttgattgat tcagatgcga ttacagttgc    4200
atggcaaatt ttctagatcc gtcgtcacat tttattttct gtttaaatat ctaaatctga    4260
tatatgatgt cgatcgacaa attctggtgg cttatacatc acttcaactg ttttcttttg    4320
gctttgtttg tcaacttggt tttcaatacg atttgtgatt tcgatcgctg aatttttaat    4380
acaagcaaac tgatgttaac cacaagcaag agatgtgacc tgccttatta acatcgtatt    4440
acttactact agtcgtattc tcaacgcaat cgttttgta tttctcacat tatgccgctt    4500
ctctactctt tattccttt ggtccacgca ttttctattt gtggcaatcc ctttcacaac    4560
ctgatttccc actttggatc atttgtctga agactctctt gaatcgttac cacttgtttc    4620
ttgtgcatgc tctgtttttt agaattaatg ataaaactat tccatagtct tgagttttca    4680
gcttgttgat tcttttgctt ttggttttct gcagaaacga tatccaccat gatccgtcga    4740
tcgtttcgca tgattgaaca agatggattg cacgcaggtt ctccggccgc ttgggtggag    4800
aggctattcg gctatgactg ggcacaacag acaatcggct gctctgatgc cgccgtgttc    4860
```

```
cggctgtcag cgcaggggcg cccggttctt tttgtcaaga ccgacctgtc cggtgccctg      4920
aatgaactac aggacgaggc agcgcggcta tcgtggctgg ccacgacggg cgttccttgc      4980
gcagctgtgc tcgacgttgt cactgaagcg ggaagggact ggctgctatt gggcgaagtg      5040
ccggggcagg atctcctgtc atctcacctt gctcctgccg agaaagtatc catcatggct      5100
gatgcaatgc ggcggctgca tacgcttgat ccggctacct gcccattcga ccaccaagcg      5160
aaacatcgca tcgagcgagc acgtactcgg atggaagccg tcttgtcga tcaggatgat       5220 ctggacgagg agcatcaggg gctcgcgcca gccgaactgt tcgccaggct caaggcgcgc      5280
atgcccgacg gcgaggatct cgtcgtgacc catggcgatg cctgcttgcc gaatatcatg      5340
gtggaaaatg gccgcttttc tggattcatc gactgtggcc ggctgggtgt ggcggaccgc      5400
tatcaggaca tagcgttggc tacccgtgat attgctgagg agcttggcgg cgaatgggct      5460
gaccgcttcc tcgtgcttta cggtatcgcc gctcccgatt cgcagcgcat cgccttctat      5520
cgccttcttg acgagttctt ctgagcggga ctctggggcc taggggatcc ttcgaaatga      5580
ccgaccaagc gacgcccaac ctgccatcac gagatttcga ttccaccgcc gccttctatg      5640
aaaggttggg cttcggaatc gttttccggg acgccggctg gatgatcctc cagcgcgggg      5700
atctcatgct ggagttcttc gcccaccccc ggatccccga tcgttcaaac atttggcaat      5760
aaagtttctt aagattgaat cctgttgccg gtcttgcgat gattatcata taatttctgt      5820
tgaattacgt taagcatgta ataattaaca tgtaatgcat gacgttattt atgagatggg      5880
tttttatgat tagagtcccg caattataca tttaatacgc gatagaaaac aaaatatagc      5940
gcgcaaacta ggataaatta tcgcgcgcgg tgtcatctat gttactagat cgggaattat      6000
ccaagactta tcacttatgt gctacattaa actatgtgtg ctccagattt atatggattt      6060
tatctatgtt taattaagac ttgtgtttac aatttttttat atttgttttt aagttttgaa      6120 tatatgttttt catgtgtgat tttaccgaac aaaaataccg gttcccgtcc gatttcgact      6180
ttaacccgac cggatcgtat cggttttcga ttaccgtatt tatcccgttc gttttcgtta      6240
ccggtatatc ccgttttcgt ttccgtcccg caagttaaat atgaaaatga aaacggtaga      6300
ggtattttac cgaccgttac cgaccgtttt catccctagc ggccgcctgc aggcatgcaa      6360
gcttctaatt aattaggata tc                                              6382
```

<210> SEQ ID NO 21
<211> LENGTH: 7046
<212> TYPE: DNA
<213> ORGANISM: Artificial
<220> FEATURE:
<223> OTHER INFORMATION: proOsRCG2::TmMYB::terAtSac66

<400> SEQUENCE: 21

```
aattacaacg gtatatatcc tgccaggaga tctctaatta attagtctag aggagctgat        60
ctcaacagtt tatttatat gatggtgtaa ccatctaata taccatgttg ctgataattt       120
ttaaccagag caattaatcg gagcatggcc ctagtgttga acaatttgca ctttcacagt       180
caggtgtaac attttgtaca ttcagcataa tggtatgctc tttgcgcttt ttcagcccctt      240 gtgtaacaca gcaggatttc aaaaacacaa ggataaaaaa acgtataaat agaatagcat      300
gccacaacaa atcatacagg attttttttaa agaaatgtta caggaaatga atccactgaa      360
tttttttttt taaaaaaaag tttggtaaca ccataggaga agtaaggaa ttaggagtca       420 cgactcatga tgaagagaaa acatgagatt taggctcatg ttaattttcc tccaaaattt      480
```

-continued

```
gttgaaatga gccattccat atgaatttca aggattttta tatgagtcat tcatttgttc      540
gtaaggacaa tataggaaca tttttcaatg aattgtaatc ctctataatt tctacagttc      600
tcctttatcc caaaggaatc tttacgtacg cacaggtaaa attgggactc ccatgatccc      660
atctttacca gaaggggcga gctagaggat tgccgtgcgt aaatttgcac ggtgctagct      720
agctagattt tgaaagtaga tgaaccgata tataacactt tgggtttcat actttcatta      780
gtccacatga acatcgaacc ctagcttaga cacggcataa atcgatcgag gcatggacgc      840
atgtatcagt atttgcatga ttgctcgatc gagattatat taccctctta cacatgcatg      900
catgggggaa taattcaaca acgtctgaat gtctgattcc tcatggaaaa ttccttgtca      960
catctctttc tctgagtact ctaacgaaca actggccatg tatgcacatg cacccccagag    1020
acaacctagc tacgtacccct gcatctgaca cccccacatg cacgtaccat tgcatctgct    1080
tacttcggat tgataatact tacagtgaac aacacggtct cttaaaaaat agctttgatt    1140
actatttcta ttataatata tatagaaata ttaacaaata tataatttta ttagatctta    1200
acaagcattt ctccatattc atccctgaaa gttggttttt ataggacgag aggagtacat    1260
atttttttaag aaaattattt tataaattat ttataatcaa atattttaaa attcgatctt    1320
aattttgtcc gaaacaacga gtattataag agcttatttg gtagagctcc aactcctaaa    1380
tttagcttca agagttagat ctgaagtaga gttatatgaa gctgcttaaa cccaactttg    1440
catgtctagt tcattttgga gatagctcta cacagctcag ctgaaattgt ttggtgaagc    1500
tagagctgtg ccaaacaggg cctccgtctg gagagaaagt agcaacgcat ccatgcaaac    1560
cactcttgct ataggctcga tcggctataa atacaagacg ccatgacacc ccaagcaaac    1620
caacccaaag caacacaagc catagcagca gagccgagta gctgagctca ctgttcgatc    1680
gatcactagc tcgctagctg cattctccac catggggctc gacgtcggcg agatcgggat    1740
gccactggat ctgggcctcg acctgcgcct cttcgttgcg aagacggctg ggaggctcgc    1800
taaggaagcc ccagctgttg atgcgtgcat cagaggcctg gaggaagaga gacgcaagat    1860
cgaggtgttc cgcagagagc tcccgctgtg cgcgaggctc ctcgcggacg tgatcgagtt    1920
catgaaggaa gaggccgcga agaggagcga gcgcagagat gctgatgaca acgacaagcg    1980
gaagtggatg tcgaccgcgc aactgtgggt gaactccagg gcgacggacg ctgccgatcc    2040
agtcaaggag caaagaagg agagcgctct ctccaagcca atgctcctgg gcggggctac    2100
cggcgtgccg atggccgttt cttgcggcgc tatgccccca ccagctgcgc cacactacct    2160
cggcagagag gataagatcg tcgggacgga gagactgcca gctctcccaa tgatctcacc    2220
cgccgccaac aggcagttct caccaccggc cgacgacagg catcaagctt tcgcggccaa    2280
gttcgcctcg gccatgccac ccccaggccc ggggctccaa gcccatgagc agcaaagcag    2340
gaagaccaga aggtgctggt ccccagagct ccatcgccac ttcgttgccg cgctccacca    2400
gctcggggggc ccacaggtgg ctaccccaaa gcaaatcagg gaggtcatga aggttgacgg    2460
cctgaccaac gatgaggtca agtcccacct ccagaagtac agactccaca accagaggtg    2520
cccgtcctct tcgtccgctt cgcatcccgt tatgctcgtg ggcgacctct gggctcacca    2580
agagcaatcc agctcgcaat caaggtcccc tgagggcccc ctgcaactga gcgtgtccgg    2640
cgtggctgtc tcagccctca cggggtccga ctcgtccgag gaagacgaca gaagcgtggg    2700
gtactccagg cggtgaaacc taatgctctt aactgagct aattatgtaa tgcacataca    2760
catatttaca tagatatgca tatttatata tagcatgtat attgtactac atgcattgct    2820
tcttaataca tgtagtaaag atatatgcaa aaatagtcga aagatttgtt tacatataaa    2880
```

```
atcaccaata tttattgtta ttgtatttc  atgaataaag taataagatt atttgtctaa  2940
tattttgatt tactagtact agaaatgaaa aggaatatgc acaatttcag cattatagtt  3000
tggtaggcaa aatggagtga gaatagagtt tcatagtata tactaaggtt cttaattgtg  3060
caaatagttg atacaagtca catgggccaa gtttgtaaat cttaaatcga aatatgcctt  3120
cttctttttt tgcatgaaaa tgctagtaat ttataagtgt gttttcaat  aagagatgct  3180
aaataccaaa attaacctag ttttcagtga gcgcttgcat tattgtgggt ggttgtacct  3240
agggtttaaa ccagggatga agtaggatg  ggaaaatccc gtaccgaccg ttatcgtata  3300
accgattttg ttagttttat cccgatcgat ttcgaacccg aggtaaaaaa cgaaaacgga  3360
acggaaacgg gatatacaaa cggtaaacgg aaacggaaac ggtagagcta gtttcccgac  3420
cgtttcaccg ggatcccgtt tttaatcggg atgatcccgt ttcgttaccg tattttctaa  3480
ttcgggatga ctgcaatatg ccagctcca  acacccatcc ataaccactg aggcccagcc  3540
catgtaagaa atacctagcg aacgctgctc tgcctctctc ccaggcggcc aggcaccaca  3600
cgagtaacag catcacacat tcacacgccg ccacgcgccc acgccggagt ccggagctag  3660
ctaattgtta ttatcaataa aagaatttt  attgttattg tgttatttgg taatttatgc  3720
ttataagtaa ttctatgatt aattgtgaat taataagact aatgaggata ataattgaat  3780
ttgattaaat taactctgcg aagccatatg tctttcacgt gagagtcacg tgatgtctcc  3840
gcgacaggct ggcacggggc ttagtattac ccccgtgccg ggatcagaga catttgacta  3900
aatgttgact tggaataata gcccttggat tagatgacac gtggacgctc aggatctgtg  3960
atgctagtga agcgcttaag ctgaacgaat ctgacggaag tgcggacaaa cgcacatgga  4020
ctatggccca ctgctttatt aaagaagtga atgacagctg tctttgcttc aagacgaagt  4080
aaagaatagt ggaaaacgcg taagaataa  gcgtactcag tacgcttcgt ggctttataa  4140
atagtgcttc gtcttattct tcgttgtatc atcaacgaag aagttaagct gatgcggccg  4200
cgaattcccc gggccaggtc cgtcgcttct cttccattc  ttctcatttt cgattttgat  4260
tcttatttct ttccagtagc tcctgctctg tgaatttctc cgctcacgat agatctgctt  4320
atactcctta cattcaacct tagatctggt ctcgattctc tgtttctctg ttttttctt  4380
ttggtcgaga atctgatgtt tgtttatgtt ctgtcaccat taataataat gaactctctc  4440
attcatacaa tgattagttt ctctcgtcta caaaacgata tgttgcattt tcactttct   4500
tcttttttc  taagatgatt tgctttgacc aatttgttta gatctttatt ttattttatt  4560
ttctggtggg ttggtggaaa ttgaaaaaaa aaaaaacag  cataaattgt tatttgttaa  4620
tgtattcatt ttttggctat ttgttctggg taaaaatctg cttctactat tgaatctttc  4680
ctggattttt tactcctatt gggtttttat agtaaaaata cataataaaa ggaaaacaaa  4740
agttttatag attctcttaa accccttacg ataaagttg  gaatcaaaat aattcaggat  4800
cagatgctct tgattgatt  cagatgcgat tacagttgca tggcaaattt tctagatccg  4860
tcgtcacatt ttattttctg tttaaatatc taaatctgat atatgatgtc gatcgacaaa  4920
ttctggtggc ttatacatca cttcaactgt tttcttttgg ctttgtttgt caacttggtt  4980
ttcaatacga tttgtgattt cgatcgctga attttaata  caagcaaact gatgttaacc  5040
acaagcaaga gatgtgacct gccttattaa catcgtatta cttactacta gtcgtattct  5100
caacgcaatc gttttgtat  ttctcacatt atgccgcttc tctactcttt attccttttg  5160
gtccacgcat tttctatttg tggcaatccc tttcacaacc tgatttccca ctttggatca  5220
```

-continued

```
tttgtctgaa gactctcttg aatcgttacc acttgtttct tgtgcatgct ctgttttta     5280 gaattaatga taaaactatt ccatagtctt gagttttcag cttgttgatt cttttgcttt     5340
tggttttctg cagaaacgat atccaccatg atccgtcgat cgtttcgcat gattgaacaa     5400
gatggattgc acgcaggttc tccggccgct tgggtggaga ggctattcgg ctatgactgg     5460
gcacaacaga caatcggctg ctctgatgcc gccgtgttcc ggctgtcagc gcaggggcgc     5520
ccggttcttt ttgtcaagac cgacctgtcc ggtgccctga tgaactaca ggacgaggca      5580 gcgcggctat cgtggctggc cacgacgggc gttccttgcg cagctgtgct cgacgttgtc     5640
actgaagcgg aagggactg gctgctattg ggcgaagtgc cggggcagga tctcctgtca      5700
tctcaccttg ctcctgccga aaagtatacc atcatggctg atgcaatgcg gcggctgcat     5760
acgcttgatc cggctacctg cccattcgac caccaagcga acatcgcat cgagcgagca      5820 cgtactcgga tggaagccgg tcttgtcgat caggatgatc tggacgagga gcatcagggg     5880
ctcgcgccag ccgaactgtt cgccaggctc aaggcgcgca tgcccgacgg cgaggatctc     5940
gtcgtgaccc atggcgatgc ctgcttgccg aatatcatgg tggaaaatgg ccgcttttct     6000
ggattcatcg actgtggccg ctgggtgtg gcggaccgct atcaggacat agcgttggct      6060
acccgtgata ttgctgagga gcttggcggc gaatgggctg accgcttcct cgtgctttac     6120
ggtatcgccg ctcccgattc gcagcgcatc gccttctatc gccttcttga cgagttcttc     6180
tgagcgggac tctggggcct aggggatcct tcgaaatgac cgaccaagcg acgcccaacc     6240
tgccatcacg agatttcgat tccaccgccg ccttctatga aaggttgggc ttcggaatcg     6300
ttttccggga cgccggctgg atgatcctcc agcgcgggga tctcatgctg gagttcttcg     6360
cccacccccg gatccccgat cgttcaaaca tttggcaata agtttctta agattgaatc      6420 ctgttgccgg tcttgcgatg attatcatat aatttctgtt gaattacgtt aagcatgtaa     6480
taattaacat gtaatgcatg acgttattta tgagatgggt ttttatgatt agagtcccgc     6540
aattatacat ttaatacgcg atagaaaaca aaatatagcg cgcaaactag gataaattat     6600
cgcgcgcggt gtcatctatg ttactagatc gggaattatc caagacttat cacttatgtg     6660
ctacattaaa ctatgtgtgc tccagattta tatggatttt atctatgttt aattaagact     6720
tgtgtttaca attttttata tttgtttta agttttgaat atatgttttc atgtgtgatt      6780
ttaccgaaca aaaataccgg ttcccgtccg atttcgactt taacccgacc ggatcgtatc     6840
ggttttcgat taccgtattt atcccgttcg ttttcgttac cggtatatcc cgttttcgtt     6900
tccgtcccgc aagttaaata tgaaaatgaa aacggtagag gtattttacc gaccgttacc     6960
gaccgttttc atccctagcg gccgcctgca ggcatgcaag cttctaatta attaggatat     7020
catttacaat tgaatatatc ctgccg                                          7046
```

<210> SEQ ID NO 22
<211> LENGTH: 6398
<212> TYPE: DNA
<213> ORGANISM: Artificial
<220> FEATURE:
<223> OTHER INFORMATION: proHvIDS2::TmMYB::terAtSac66

<400> SEQUENCE: 22

```
aattacaacg gtatatatcc tgccaggaga tctctaatta attagtctag aggaaacatt      60 ttaatgtgt tttgtatag tgtcttaaaa aatacttgtt tgtttaata ttcaatagta        120 aaaggaaca caaataataa aagaaaaac atgaaaaaag aaatacaata aaacaggctt       180
gtgattccct cccgcgtggg acggcggttc ctacgaggag gtgttggggc accccgggca     240
```

```
atcggaggta ttctcttcgt cacggtttaa aaggcatgct tggaaattat ctagaaccta    300
gatggttatt gattagttat gagatggact aaaaaatagc agtcacacta cgcatacata    360
tagaagtagt ataacagagt actataatta gctgctatga gtaatgaaat gcaccctaaa    420
taatcttgtc tatcatggaa atgcacgtaa atttaaccgt gtcttctaaa tagtgacgga    480
aggagcacca aatacattgc agtggagtct cgggccagtt aactttgacc ctcattgata    540
aaaatgaata ataacttgg  actatgacta gcaaaactag ccggacaatt tgacctaaac    600
aggctagcta ggacccaatt acaaaagcaa catggactaa cttggactcc acacctaccc    660
gaagtagcac atgaaaagga ttaaccgact cattctggac ttttataatc taataatcaa    720
ccgagaggcc atgcatccgt ctagtatata acagtatata taataacaat ccatactaga    780
cgacgaggac gatttgaacg gcaagtttca cgctgtcact cccactctcg ctctcatttt    840
attaatcact aacaaacgca tgatttgatc agacacccaa aataggaata ggagatgcta    900
tcatcaagca tgcttcttgc tgcccagagc atcccacgac tacaaaacac ggctggccgg    960
aggattataa cacgatcgag cgaccaatcc aagcacctac gcactcttct ttgctctcat   1020
cctctagcta gctaactagc tctcttggat catcctctcc accatggggc tcgacgtcgg   1080
cgagatcggg atgccactgg atctgggcct cgacctgcgc ctcttcgttg cgaagacggc   1140
tgggaggctc gctaaggaag ccccagctgt tgatgcgtgc atcagaggcc tggaggaaga   1200
gagacgcaag atcgaggtgt tccgcagaga gctcccgctg tgcgcgaggc tcctcgcgga   1260
cgtgatcgag ttcatgaagg aagaggccgc gaagaggagc gagcgcagag atgctgatga   1320
caacgacaag cggaagtgga tgtcgaccgc gcaactgtgg gtgaactcca gggcgacgga   1380
cgctgccgat ccagtcaagg agcaaaagaa ggagagcgct ctctccaagc caatgctcct   1440
gggcggggct accggcgtgc cgatggccgt ttcttgcggc gctatgcccc caccagctgc   1500
gccacactac ctcggcagag aggataagat cgtcggacg  gagagactgc cagctctccc   1560
aatgatctca cccgccgcca acaggcagtt ctcaccaccg gccgacgaca ggcatcaagc   1620
tttcgcggcc aagttcgcct cggccatgcc accccaggc  ccgggctcc  aagcccatga   1680
gcagcaaagc aggaagacca aaggtgctg  gtccccagag ctccatcgcc acttcgttgc   1740
cgcgctccac cagctcgggg gcccacaggt ggctacccca aagcaaatca gggaggtcat   1800
gaaggttgac ggcctgacca cgatgaggt  caagtcccac ctccagaagt acagactcca   1860
caaccagagg tgcccgtcct cttcgtccgc ttcgcatccc gttatgctcg tgggcgacct   1920
ctgggctcac caagagcaat ccagctcgca atcaaggtcc cctgagggcc ccctgcaact   1980
gagcgtgtcc ggcgtggctg tctcagccct cacggggtcc gactcgtccg aggaagacga   2040
cagaagcgtg gggtactcca ggcggtgaaa cctaaatgct cttaactgag ctaattatgt   2100
aatgcacata cacatatttta catagatatg catatttata tatagcatgt atattgtact   2160
acatgcattg cttcttaata catgtagtaa agatatatgc aaaaatagtc gaaagatttg   2220
tttacatata aaatcaccaa tatttattgt tattgtattt tcatgaataa agtaataaga   2280
ttatttgtct aatattttga tttactagta ctagaaatga aaaggaatat gcacaatttc   2340
agcattatag tttggtaggc aaaatggagt gagaatagag tttcatagta tatactaagg   2400
ttcttaattg tgcaaatagt tgatacaagt cacatgggcc aagtttgtaa atcttaaatc   2460
gaaatatgcc ttcttctttt tttgcatgaa aatgctagta atttataagt gtgttttttca   2520
ataagagatg ctaaatacca aaattaacct agttttcagt gagcgcttgc attattgtgg   2580
```

-continued

```
gtggttgtac ctagggttta aaccagggat gaaagtagga tgggaaaatc ccgtaccgac    2640
cgttatcgta taaccgattt tgttagtttt atcccgatcg atttcgaacc cgaggtaaaa    2700
aacgaaaacg gaacggaaac gggatataca acggtaaac ggaaacggaa acggtagagc     2760
tagtttcccg accgtttcac cgggatcccg tttttaatcg ggatgatccc gtttcgttac    2820 cgtatttctct aattcgggat gactgcaata tggccagctc caacacccat ccataaccac   2880
tgaggcccag cccatgtaag aaatacctag cgaacgctgc tctgcctctc tcccaggcgg    2940
ccaggcacca cacgagtaac agcatcacac attcacacgc cgccacgcgc ccacgccgga    3000
gtccggagct agctaattgt tattatcaat aaaagaattt ttattgttat tgtgttattt    3060
ggtaatttat gcttataagt aattctatga ttaattgtga attaataaga ctaatgagga    3120
taataattga atttgattaa attaactctg cgaagccata tgtctttcac gtgagagtca    3180
cgtgatgtct ccgcgacagg ctggcacggg gcttagtatt accccgtgc cgggatcaga     3240 gacatttgac taaatgttga cttggaataa tagcccttgg attagatgac acgtggacgc    3300
tcaggatctg tgatgctagt gaagcgctta agctgaacga atctgacgga agtgcggaca    3360
aacgcacatg gactatggcc cactgctta ttaaagaagt gaatgacagc tgtctttgct     3420
tcaagacgaa gtaaagaata gtggaaaacg cgtaaagaat aagcgtactc agtacgcttc    3480
gtggctttat aaatagtgct tcgtcttatt cttcgttgta tcatcaacga agaagttaag    3540
ctgatgcggc cgcgaattcc ccgggccagg tccgtcgctt ctcttccatt tcttctcatt    3600
ttcgattttg attcttattt ctttccagta gctcctgctc tgtgaatttc tccgctcacg    3660
atagatctgc ttatactcct tacattcaac cttagatctg gtctcgattc tctgtttctc    3720 tgttttttc ttttggtcga gaatctgatg tttgtttatg ttctgtcacc attaataata    3780
atgaactctc tcattcatac aatgattagt ttctctcgtc tacaaaacga tatgttgcat    3840 tttcacttttt cttctttttt tctaagatga tttgctttga ccaatttgtt tagatcttta    3900
ttttatttta ttttctggtg ggttggtgga aattgaaaaa aaaaaaaaac agcataaatt    3960
gttatttgtt aatgtattca tttttggct atttgttctg ggtaaaaatc tgcttctact     4020
attgaatctt tcctggattt tttactccta ttgggttttt atagtaaaaa tacataataa    4080
aaggaaaaca aaagttttat agattctctt aaacccctta cgataaaagt tggaatcaaa    4140
ataattcagg atcagatgct ctttgattga ttcagatgcg attacagttg catggcaaat    4200
tttctagatc cgtcgtcaca ttttatttc tgtttaaata tctaaatctg atatatgatg     4260
tcgatcgaca aattctggtg gcttatacat cacttcaact gttttctttt ggctttgttt    4320
gtcaacttgg ttttcaatac gatttgtgat ttcgatcgct gaattttaa tacaagcaaa     4380 ctgatgttaa ccacaagcaa gagatgtgac ctgccttatt aacatcgtat tacttactac    4440
tagtcgtatt ctcaacgcaa tcgttttgt atttctcaca ttatgccgct tctctactct     4500
ttattccttt tggtccacgc attttctatt tgtggcaatc cctttcacaa cctgatttcc    4560
cactttggat catttgtctg aagactctct tgaatcgtta ccactgtttt cttgtgcatg    4620
ctctgttttt tagaattaat gataaaacta ttccatagtc ttgagttttc agcttgttga    4680
ttcttttgct tttggttttc tgcagaaacg atatccacca tgatccgtcg atcgtttcgc    4740
atgattgaac aagatggatt gcacgcaggt tctccggccg cttgggtgga gaggctattc    4800
ggctatgact gggcacaaca gacaatcggc tgctctgatg ccgccgtgtt ccggctgtca    4860 gcgcagggc gcccggttct ttttgtcaag accgacctgt ccggtgccct gaatgaacta    4920
caggacgagg cagcgcggct atcgtggctg gccacgacgg gcgttccttg cgcagctgtg    4980
```

```
ctcgacgttg tcactgaagc gggaagggac tggctgctat tgggcgaagt gccggggcag    5040
gatctcctgt catctcacct tgctcctgcc gagaaagtat ccatcatggc tgatgcaatg    5100
cggcggctgc atacgcttga tccggctacc tgcccattcg accaccaagc gaaacatcgc    5160
atcgagcgag cacgtactcg gatggaagcc ggtcttgtcg atcaggatga tctggacgag    5220
gagcatcagg ggctcgcgcc agccgaactg ttcgccaggc tcaaggcgcg catgcccgac    5280
ggcgaggatc tcgtcgtgac ccatggcgat gcctgcttgc cgaatatcat ggtggaaaat    5340
ggccgctttt ctggattcat cgactgtggc cggctgggtg tggcggaccg ctatcaggac    5400
atagcgttgg ctacccgtga tattgctgag gagcttggcg gcgaatgggc tgaccgcttc    5460
ctcgtgcttt acggtatcgc cgctcccgat cgcagcgca tcgccttcta tcgccttctt     5520
gacgagttct tctgagcggg actctggggc ctaggggatc cttcgaaatg accgaccaag    5580
cgacgcccaa cctgccatca cgagatttcg attccaccgc cgccttctat gaaaggttgg    5640
gcttcggaat cgtttccgg gacgccggct ggatgatcct ccagcgcggg gatctcatgc     5700
tggagttctt cgcccacccc cggatccccg atcgttcaaa catttggcaa taaagtttct    5760
taagattgaa tcctgttgcc ggtcttgcga tgattatcat ataatttctg ttgaattacg    5820
ttaagcatgt aataattaac atgtaatgca tgacgttatt tatgagatgg gtttttatga    5880
ttagagtccc gcaattatac atttaatacg cgatagaaaa caaatatag cgcgcaaact      5940
aggataaatt atcgcgcgcg gtgtcatcta tgttactaga tcgggaatta ccaagactt      6000
atcacttatg tgctacatta aactatgtgt gctccagatt tatatggatt ttatctatgt    6060
ttaattaaga cttgtgttta caattttta tatttgtttt taagttttga atatatgttt     6120
tcatgtgtga ttttaccgaa caaaaatacc ggttcccgtc cgatttcgac tttaacccga    6180
ccggatcgta tcggttttcg attaccgtat ttatcccgtt cgttttcgtt accggtatat    6240
cccgtttcg tttccgtccc gcaagttaaa tatgaaaatg aaaacggtag aggtatttta     6300
ccgaccgtta ccgaccgttt tcatccctag cggccgcctg caggcatgca agcttctaat    6360
taattaggat atcatttaca attgaatata tcctgccg                             6398
```

<210> SEQ ID NO 23
<211> LENGTH: 3959
<212> TYPE: DNA
<213> ORGANISM: Artificial
<220> FEATURE:
<223> OTHER INFORMATION: proPR110_intSH1_synMYB TaMod_terSac66

<400> SEQUENCE: 23

```
tcgacgctac tcaagtggtg ggaggccacc gcatgttcca acgaagcgcc aaagaaagcc      60
ttgcagactc taatgctatt agtcgcctag gatatttgga atgaaaggaa ccgcagagtt     120
tttcagcacc aagagcttcc ggtggctagt ctgatagcca aaattaagga ggatgccaaa    180
acatgggtct tggcgggcgc gaaacaccct gataggtggc ttacctttta acatgttcgg    240
gccaaaggcc ttgagacggt aaagtttct atttgcgctt gcgcatgtac aatttttattc    300
ctctattcaa tgaaattggt ggctcactgg ttcattaaaa aaaaagaat ctagcctgtt     360
cgggaagaag aggattttgt tcgtgagaga gagagagaga gagagagaga gagagagaga    420
gaaggaggag gaggattttc aggcttcgca ttgcccaacc tctgcttctg ttggcccaag    480
aagaatccca ggcgcccatg ggctggcagt ttaccacgga cctacctagc ctaccttagc    540
tatctaagcg ggccgaccta gtagccacgt gcctagtgta gattaaagtt gccgggccag    600
```

```
caggaagcca cgctgcaatg gcatcttccc ctgtccttcg cgtacgtgaa acaaaccca      660 ggtaagctta gaatcttctt gcccgttgga ctgggacacc caccaatccc accatgcccc    720
gatattcctc cggtctcggt tcatgtgatg tcctctcttg tgtgatcacg gagcaagcat    780
tcttaaacgg caaagaaaaa tcaccaactt gctcacgcag tcacgctgca ccgcgcgaag    840
cgacgcccga taggccaaga tcgcgagata aaataacaac caatgatcat aaggaaacaa    900
gcccgcgatg tgtcgtgtgc agcaatcttg gtcatttgcg ggatcgagtg cttcacagct    960
aaccaaatat tcggccgatg atttaacaca ttatcagcgt agatgtacgt acgatttgtt   1020
aattaatcta cgagccttgc tagggcaggt gttctgccag ccaatccaga tcgccctcgt   1080
atgcacgctc acatgatggc agggcagggt tcacatgagc tctaacggtc gattaattaa   1140
tcccggggct cgactataaa tacctcccta atcccatgat caaaaccatc tcaagcagcc   1200
taatcatctc cagctgatca agagctctta attagctagc tagtgattag ctgcgcttgt   1260
gatctctaga gtcgagatcc gtcccgacca ttggggtatg cttgctgcct tgctctcctg   1320
ttcatctccg tgctaaacct ctgtcctctg ggtgggtttt gctgggatt ttgagctaat    1380 ctgctggtcc cggtagaaaa gatcatgtcc cctgacgagc tcaagcgctc gccttagccg   1440
cgtccttgcc ccccgccatt ttttgcggtt tcggtgtgtt cccgtgactc gccgggtgcg   1500
tcatcgcctg aatcttgtct gggctctgct gacatgttct tggctagttg ggtttataga   1560
ttcctctgat ctaaaccgtg cctgtgctgc gcacagaact ctcccctgtc ctttcctggg   1620
gttttggtta cgtggtggta gtaagcttgg atttgcacat ggataaagtt gttctaagct   1680
ccgtgggttc cttgagatct tgctgttatt gcgtgccgtg ctcactttt ttgcaatccg    1740 aggaatgaat ttgtcgttta ctcgttttgg tggattatta gcgcgaaaaa aaaactcttt   1800
tttttttttg ttcttttact acgaaaagca tcttcttgga ttttgctatc ttcttttact   1860
acgaaaaact cttgagtcta ggaatttgaa tttgtgatgt ccattcttgc agtgcgctgt   1920
gctttattgg gaagccaaat cctattattt tctgcctcta gggtctgaat ggaatcagta   1980
ctcttgagac agaaaatcaa tccaatcaag ttgatttctt tctttaaaaa tattatcaca   2040
gaactaagtg cttgtgcgga atcagtactg gcttttgttt ggtggaggat caatacttgc   2100
ttttgtttgg gggtggcaac tgttttgcta taagattcca tgtgttcctg ttgagatgaa   2160
tcatatatag tatagctgca tactacaaat ctgttttttca aatttaggtt gctttggcat   2220
gatctatttt tttgtcagac agactttcta agtggtagct cttgatttct tgttcttgta   2280
caactggtgc tgctgaatct tgaccgtata gctcgaattg cagtattctg aaccatcgac   2340
cgacctcgac ggtatcgata agcttgatag cttgatatca caagtttgta caaaaaagca   2400
ggctccacca tgggcctcga cgtcggcgag atcggtatgc cgctcgattt gggcctcgac   2460
ctcaggctct tcgtggccaa gacagccggt cggcttgcga aggaggcccc agccgtcgac   2520
gcctgcatcc ggggcctcga ggaggagcgc cgtaagatcg aggtctttcg cagggagctg   2580
cccttgtgcg ctcggcttct cgcggacgtc attgagttca tgaaggaaga ggcggcaaag   2640
aggagtgagc gtcgtgatgc ggacgacaac gacaagcgca agtggatgtc gaccgcccaa   2700
ttgtgggtta actcaaggc gaccgacgca gccgacctg tcaaggagca aaagaaggag     2760
tccgccctct caaagcctat gctcttgggg ggcgctaccg gggtcccgat ggccgttagc   2820
tgcggcgcta tgcccctcc agccgcaccc cactacctgg gtcgcgaaga caagatcgtc   2880
ggaacggagc gtctccccgc gttgccgatg atttcgccgg ctgccaacag gcagttctct   2940
ccgccagctg acgataggca tcaagccttc gccgcgaagt tcgcgtcggc catgccgccc   3000
```

```
ccaggccctg gactgcaggc ccatgagcag caaagcagga agactagacg gtgctggtct    3060
cccgagttgc accgccattt tgttgcggcc ctccaccagc tcggcggtcc tcaggtggcc    3120 accccccaagc aaatcaggga ggtcatgaag gttgacgggc ttacgaacga cgaggtcaag    3180
tcccacctcc agaagtacag acttcacaac caaaggtgtc catcctcgtc gtcggcctcc    3240
cacccagtga tgcttgtggg cgacctttgg gcccaccaag agcagagttc cagccagagc    3300
cggtccccag agggcccact gcagctctct gtttcgggcg tcgccgtctc agcactgacc    3360
ggcagcgaca gcagtgagga ggacgacaga tccgtgggct actcccgccg ttaatctaga    3420
cccagctttc ttgtacaaag tggtgatatc ctaaatgctc ttaactgagc taattatgta    3480
atgcacatac acatatttac atagatatgc atatttatat atagcatgta tattgtacta    3540
catgcattgc ttcttaatac atgtagtaaa gatatatgca aaaatagtcg aaagatttgt    3600
ttacatataa aatcaccaat atttattgtt attgtatttt catgaataaa gtaataagat    3660
tatttgtcta atatttttgat ttactagtac tagaaatgaa aaggaatatg cacaatttca    3720
gcattatagt ttggtaggca aaatggagtg agaatagagt ttcatagtat atactaaggt    3780
tcttaattgt gcaaatagtt gatacaagtc acatgggcca agtttgtaaa tcttaaatcg    3840
aaatatgcct tcttcttttt ttgcatgaaa atgctagtaa tttataagtg tgttttttcaa    3900 taagagatgc taaataccaa aattaaccta gttttcagtg agcgcttgca ttattgtgg    3959
```

```
<210> SEQ ID NO 24
<211> LENGTH: 57
<212> TYPE: PRT
<213> ORGANISM: Artificial
<220> FEATURE:
<223> OTHER INFORMATION: MYB domain
<220> FEATURE:
<221> NAME/KEY: VARIANT
<222> LOCATION: (3)..(3)
<223> OTHER INFORMATION: Xaa is A, S or T
<220> FEATURE:
<221> NAME/KEY: VARIANT
<222> LOCATION: (9)..(9)
<223> OTHER INFORMATION: Xaa is T or P
<220> FEATURE:
<221> NAME/KEY: VARIANT
<222> LOCATION: (10)..(10)
<223> OTHER INFORMATION: Xaa is D or E
<220> FEATURE:
<221> NAME/KEY: VARIANT
<222> LOCATION: (14)..(14)
<223> OTHER INFORMATION: Xaa is H, Q, R, L or K
<220> FEATURE:
<221> NAME/KEY: VARIANT
<222> LOCATION: (20)..(20)
<223> OTHER INFORMATION: Xaa is H, Q, R, N or D
<220> FEATURE:
<221> NAME/KEY: VARIANT
<222> LOCATION: (21)..(21)
<223> OTHER INFORMATION: Xaa is E or Q
<220> FEATURE:
<221> NAME/KEY: VARIANT
<222> LOCATION: (36)..(36)
<223> OTHER INFORMATION: Xaa is L or V
<220> FEATURE:
<221> NAME/KEY: VARIANT
<222> LOCATION: (38)..(38)
<223> OTHER INFORMATION: Xaa is K or Q

<400> SEQUENCE: 24

Arg Lys Xaa Arg Arg Cys Trp Ser Xaa Xaa Leu His Arg Xaa Phe Val
1               5                   10                  15

Ala Ala Leu Xaa Xaa Leu Gly Gly Pro Gln Val Ala Thr Pro Lys Gln
```

```
                    20                  25                  30
Ile Arg Glu Xaa Met Xaa Val Asp Gly Leu Thr Asn Asp Glu Val Lys
        35                  40                  45

Ser His Leu Gln Lys Tyr Arg Leu His
    50                  55

<210> SEQ ID NO 25
<211> LENGTH: 18
<212> TYPE: DNA
<213> ORGANISM: Artificial
<220> FEATURE:
<223> OTHER INFORMATION: Forward primer

<400> SEQUENCE: 25
ttttctcccc ctgccgac                                                     18

<210> SEQ ID NO 26
<211> LENGTH: 20
<212> TYPE: DNA
<213> ORGANISM: Artificial
<220> FEATURE:
<223> OTHER INFORMATION: Reverse primer

<400> SEQUENCE: 26
gtcataccgt tcgtcgtcca                                                   20
```

METHOD FOR PLANT IMPROVEMENT

CROSS-REFERENCE TO RELATED APPLICATIONS

This application is a national stage application (under 35 U.S.C. § 371) of PCT/EP2016/068246, filed Jul. 29, 2016, which claims benefit of European Application No. 15306282.3, filed Aug. 10, 2015, which are incorporated herein by reference in their entireties.

The invention disclosed herein provides a method for producing transgenic plant with increased yield compared to non transgenic control plants. The present invention further relates to a nucleic construct increasing yield of the transgenic plants, and cell, seed and plant comprising the nucleic construct and method of producing and using such cell, seed and plant.

In agriculture, yield is the amount of product harvested from a given acreage (eg weight of seeds per unit area). It is often expressed in metric quintals (1 q=100 kg) per hectare in the case of cereals. It is becoming increasingly important to improve the yield of seed crops to feed an expanding population and, more recently, for biofuel production. One strategy to increase the yield is to increase the seed size, provided that there is not a concomitant decrease in seed number.

One important issue to be achieved in transgenic crop is obtaining plants capable of maintaining or increasing yield under stress conditions compared to normal conditions. Stress conditions can correspond for example to abiotic stress like light stress, extreme temperatures (heat, cold and freezing), drought (lack of precipitations) or soil contamination by salt. All these environmental stresses can more or less impair plant development growth and ultimately yield.

Another challenge for crop development and cultivation is the efficient use of nutrients.

Nitrogen (N) is one of the most important nutrients required for crop growth and development and more generally, N is an essential component of the yield. As N deficiency is known to affect yield in crop production, N fertilizer have increasingly been used worldwide on crop fields. However, it is becoming a necessity to developing crops that require lower input of N fertilizers while producing higher yields, for economic reasons and for fround and ecosystems protection. Consequently, it is important to understanding plant response to N deficiency stress.

Major enzyme, transporter and transcription factors coding genes have been cloned and shown to drive nitrogen economy in plants (for review Mc Allister et al, 2012, Plant Biotechnology Journal, pp 1-15).

The family of transcription factors MYB is a gene family very complex. Many different genes have been identified so far in various plant species, as for example, 204 genes in *Arabidopsis*, 218 genes in rice and 180 genes in *Brachypodium* (Chen et al., 2006; Velasco et al., 2007; Wilkins et al., 2009; International *Brachypodium* Initiative, 2010).

In wheat, Zhang et al identified 60 genes belonging to the MYB family genes. One member belongs to R1R2R3-MYB, 22 to R2R3-MYB and 37 to the MYB-related subfamilies (Zhang L., Zhao G., Jia J., Liu X., Kong X., Molecular characterization of 60 isolated wheat MYB genes and analysis of their expression during abiotic stress, 2012, Journal of Experimental Botany, Vol. 63, N° 1 203-2014). The authors analyzed the expression of the MYB genes in different wheat tissues and also under different stress conditions (treatments with polyethylene glycol, high salt, ABA and under low temperature). It has to be noted that none of the stress conditions were related to nitrogen deficiency conditions.

Patent applications US20140115737, US 2011/0277190 and US 2008/0148432 describe sequence showing homologies with MYB-related protein. However, there is no description of the role of this protein in yield improvement under normal or nitrogen deficiency conditions.

The inventors have now found that the overexpression of a MYB-related plays a major role in driving yield increase either in normal or under nitrogen deficiency conditions.

SUMMARY OF THE INVENTION

The invention disclosed herein provides a method for producing a plant, particular a monocotyledon plant, with increased yield in normal and/or nitrogen stress conditions as compared to a wild type not transformed plant.

The method comprises the step of transforming a plant with a gene coding for a MYB related protein, under the control of a promoter that is functional (i.e. that is capable of driving expression of the gene) in the root of said plant. In a specific embodiment, said promoter is not the natural promoter of said MYB-related gene (ie is a heterologous promoter with regards to said MYB-related gene). It is also to be noted that such promoter is not a constitutive promoter, i.e. active in all tissues of the plant.

Multiple promoters functional in the root have been described in the art, for various plants.

As a matter of illustration, one can cite the following promoters

IDS2 promoter from barley (Kobayashi et al., 2003) depicted as SEQ ID NO: 9 isoflavone synthase gene promoters (IFS1 and IFS2) from soybean (Subramanian et al., 2004), MsPRP2 promoter from alfalfa (Winicov et al., 2004)

Pyk10, NIP2 and Pht1 promoters from *Arabidopsis* (Mizutani et al., 2006; Mudge et al., 2003; Nitz et al., 2001)"

Several root-specific promoters such as tobacco TobRB7, strawberry FaRB7, tomato LcRB7, western white pine PsPR10 and PmPR10, and others have been isolated (Nan et al. 2002 (X. Xu et al. 2010)(Liu et Ekramoddoullah 2003)(Vaughan et al. 2006)(Kirch et al. 2000).

Maize ZmTIP2-3 (Lopez et al. 2004), depicted as SEQ ID NO: 11.

GmTIP (Chen et al. 2015)

GmPRP1 and GmPRP2 exhibit root-specific expression (Suzuki, Fowler, et Tierney 1993)(Hong, Nagao, et Key 1989)(Chen et al. 2014)

rRSP1, rRSP3, and rRSP5 (HUANG et al. 2015)

Os03g01700 depicted as SEQ ID NO: 12 and Os02g37190, (Li et al. 2013).

proOsRCG2 is a promoter from *Oryza sativa* (rice) highly expressed only in root tissues according to (Y. Xu et al. 1995) and depicted as SEQ ID NO: 10 pR110 promoter, also designated as RCc3 promoter (Plant Mol Biol. 1995 January; 27(2):237-48) and depicted as SEQ ID NO: 13

*Medicago* phosphate transporter: Xiao et al., 2008, Plant Biol (Stuttg). 2008 July:8(4)439-49

Tobacco auxin-inducible gene: Van der Zaal et al Plant Mol Biol. 16, 983, 1991.

tobacco root-specific genes: Conkling, et al, Plant Physiol. 93, 1203: 1990

*B. napus* G1-3b gene: U.S. Pat. No. 5,401,836

SbPRP1: Suzuki et al., Plant Mol, Biol. 21: 109-119, 1993.

LRX1: Baumberger et al, 2001, Genes & Dev, 15; 1128

B. napus BTG-26 Brassica US 20050044585 class I patatin gene (potato): Liu et al, Plant Mol, Biol. 17 (6): 1139-1154

ALFS (*Arabidopsis*): Diener et al. (2001, Plant Cell 13:1625)

Particular interesting promoters are the ones depicted as SEQ ID NO: 9, SEQ ID NO: 10, SEQ ID NO: 11, SEQ ID NO: 12 or SEQ ID NO: 13.

The invention thus relates to a nucleic acid construct comprising
a) a promoter functional in the root, operably linked to
b) a nucleic acid coding for MYB related protein.

Said nucleic acid may also be called an "expression cassette".

In the context of the invention, a MYB related protein is defined as being a protein, the sequence of which
presents at least 60% identity with SEQ ID NO:2, and
contains a MYB domain sequence.

Said identity is calculated by using the algorithm of Needleman and Wunsch (J Mol Biol. 1970 March; 48(3): 443-53), using the following parameters: matrix BLOSUM62, gapopen penalty: 10, Gapextension penalty: 0.5.

In preferred embodiments, said MYB related protein presents an identity equal or above 70%, preferably, equal or above 80% more preferably equal or above 90%, more preferably equal or above 92%, more preferably equal or above 93%, more preferably equal or above 94%, more preferably equal or above 95%, more preferably equal or above 96%, more preferably equal or above 97%, more preferably equal or above 98%, more preferably equal or above 99% more preferably equal or above 99.5%, more preferably equal or above 99.8% with SEQ ID NO: 2

As indicated above, a "MYB-related protein" designates a protein that is harboring a MYB domain, consisting in one MYB repeat. A MYB repeat is about 52 to 56 amino acids in length and is able to form a hydrophobic core. Each MYB repeat forms three alpha-helixes.

Such a MYB domain sequence is represented by SEQ ID NO: 24: RKX$_1$RRCWSX$_2$X$_3$LHRX$_4$FVAALX$_5$X$_6$LGGPQ-VATPKQIREX$_7$MX$_8$VDGLTNDEVKSH LQKYRLH, whereas:
X$_1$ is A, S or T
X$_2$ is T or P
X$_3$ is D or E
X$_4$ is H, Q, R, L or K
X$_5$ is H, Q, R, N or D
X$_6$ is E or Q
X$_7$ is L or V, and
X$_8$ is K or Q.

Furthermore, it is foreseen that the first amino-acid of such MYB domain sequence is located at a position situated between 200 and 240, starting from the first amino-acid of the MYB-related protein.

In a preferred embodiment, the full sequence of said MYB related protein contains between 330 and 400 amino acids.

It is to be noted that the Needleman and Wunsch algorithm, not only provides a percentage of identity between two amino-acid sequences, but also provides a percentage of similarity between said two sequences.

Two amino-acids are similar when they have similar physico-chemical properties (see https://biokamikazi.files.wordpress.com/2013/06/aminoacid_and_substitutions.pdf, which also describes possible substitutions of amino acids):

Amino-acids are similar, for example if they are aromatic (F, Y, W, H), hydrophobic (V, I, L, M, C, A, F, Y, W, H, R, G, K), aliphatic (A, P, V, I, L), polar and charged positive (R, K, H), polar and charged negative (D, E), polar and neutral (H, N, Q, T, S, Y), or small. (A, T, S, C, G, V).

Various similarity matrixes exist for comparing amino acid sequences, such as BLOSUM62, PAM250 or GONNET similarity matrix. The preferred similarity matrix is BLOSUM62.

Some promoters functional in the root have described above. Other promoters can easily be used and identified by the person skilled in the art.

A promoter "functional in a given tissue" of a plant is a promoter that allows expression of a nucleic acid sequence operatively linked to it in said given tissue of said plant.

In a preferred embodiment, said promoter is predominantly functional in the roots, i.e. said promoter can be active in other tissues than the roots, but the principal expression of a nucleic acid sequence encoding a protein operatively linked to it is in the roots. This can be verified, using various techniques known by the person skilled in the art, such as quantification of the RNA expression of said nucleic acid sequence in various tissues by Northern blot, or of the protein expression in various tissues by Western blot. After quantification of the mRNA of the gene in all tissues, mRNA quantity in the roots amounts to 80% or more of the total mRNA quantified.

The promoter can be specific to the roots. A promoter specific to a given tissue is active exclusively in said tissue, i.e. it is not possible to detect expression of a nucleic acid sequence encoding a protein operatively linked to it in other tissues than said given tissue.

A preferred promoter is any one of the promoter listed above. It is to be noted that, although the references provide sequences used to define the specific promoters, a sequence that is at least 90% identical, preferably at least 95% identical, more preferably at least 96% identical, more preferably at least 97% identical, more preferably at least 98% identical, more preferably at least 99% identical, more preferably at least 99.5% identical, more preferably at least 99.7% identical, more 15 preferably at least 99.9% identical, more preferably at least 99.95% identical to the sequences provided in these references or in the present application can also be considered as being such promoter. This is because it is known that it is possible to change or delete (especially in the 5' end) a few nucleic acids in a promoter without modifying its pattern of expression.

Sequences of particular interest are the ones that also present an e-value that is lower than 1×e-150 when performing a blastn with any root-specific promoter as described in the literature above, or in the application, as a query, and the following parameters: sequences
Expect threshold: 10
Word size: 28
Max matches in a query range: 0
Scoring Parameters Match/Mismatch Scores: 1, −2
Gap Costs: Linear Such sequences can easily be checked for their ability to induce expression of a gene in the roots. Comparing the patterns of expression of a modified promoter and of the promoter depicted in the documents cited above or in this application can be performed using any reporter gene known in the art, such as the luciferase, GUS or GFP genes.

In particular, one can use the *Triticum monoccocum* protein, the sequence of an allele of which is depicted by SEQ ID NO: 2, the sequence of the cDNA being depicted by SEQ ID NO: 1.

One can also use a *Brachypodium distachyon* protein, the sequence of an allele of which is represented by SEQ ID NO: 3.

One can also use a maize (*Zea mays*) protein, the sequence of an allele of which is represented by SEQ ID NO: 4, SEQ ID NO: 5 or SEQ ID NO: 6.

One can also use a rice (*Oryza sativa*) protein, the sequence of an allele of which is represented by SEQ ID NO: 7.

One can also use a *Triticum aestivum* protein, the sequence of an allele of which is represented by SEQ ID NO: 8.

It is also to be noted that the sequences SEQ ID NO: 2 to SEQ ID NO: 8 represent and exemplify alleles of MYB-related proteins in various plants. There exists different other alleles of this protein in said plants, and different other MYB-related proteins in said plants or in other plants, which all possess the same activity than this protein, and can equivalently be used in the above-identified nucleic acid construct.

These proteins may be identified, by applying the BLASTP program (especially the BLASTP 2.2.29 program) (Altschul et al, (1997), Nucleic Acids Res. 25:3389-3402; Altschul et al, (2005) FEBS J. 272:5101-5109) to any of SEQ ID NO: 2 to SEQ ID NO: 8, using the following algorithm parameters:

Expected threshold: 10
Word size: 3
Max matches in a query range: 0
Matrix: BLOSUM62
Gap Costs: Existence 11, Extension 1.
Compositional adjustments: Conditional compositional score matrix adjustment
No filter for low complexity regions The proteins that can equivalently be used in the context of the above construct are preferably the ones, the sequence of which presents a Max score above 500, and a E value of 0.0 or less than $1e^{-170}$, with at least one sequence chosen in the group consisting of SEQ ID NO: 2, SEQ ID NO: 3, SEQ ID NO: 4, SEQ ID NO: 5, SEQ ID NO: 6; SEQ ID NO: 7 and SEQ ID NO: 8.

The sequence of proteins usable in the above construct would preferably present an identity (as indicated by the Needleman and Wunsch algorithm) equal or above 70%, preferably, equal or above 80% more preferably equal or above 90%, more preferably equal or above 92%, more preferably equal or above 93%, more preferably equal or above 94%, more preferably equal or above 95%, more preferably equal or above 96%, more preferably equal or above 97%, more preferably equal or above 98%, more preferably equal or above 99% more preferably equal or above 99.5%, more preferably equal or above 99.8% with SEQ ID NO: 2.

The sequence of proteins usable in the above construct would also preferably present an identity (as indicated by the Needleman and Wunsch algorithm) equal or above 70%, preferably, equal or above 80% more preferably equal or above 90%, more preferably equal or above 92%, more preferably equal or above 93%, more preferably equal or above 94%, more preferably equal or above 95%, more preferably equal or above 96%, more preferably equal or above 97%, more preferably equal or above 98%, more preferably equal or above 99% more preferably equal or above 99.5%, more preferably equal or above 99.8% with SEQ ID NO: 3.

The sequence of proteins usable in the above construct would also preferably present an identity (as indicated by the Needleman and Wunsch algorithm) equal or above 70%, preferably, equal or above 80% more preferably equal or above 90%, more preferably equal or above 92%, more preferably equal or above 93%, more preferably equal or above 94%, more preferably equal or above 95%, more preferably equal or above 96%, more preferably equal or above 97%, more preferably equal or above 98%, more preferably equal or above 99% more preferably equal or above 99.5%, more preferably equal or above 99.8% with SEQ ID NO: 4.

The sequence of proteins usable in the above construct would also preferably present an identity (as indicated by the Needleman and Wunsch algorithm) equal or above 70%, preferably, equal or above 80% more preferably equal or above 90%, more preferably equal or above 92%, more preferably equal or above 93%, more preferably equal or above 94%, more preferably equal or above 95%, more preferably equal or above 96%, more preferably equal or above 97%, more preferably equal or above 98%, more preferably equal or above 99% more preferably equal or above 99.5%, more preferably equal or above 99.8% with SEQ ID NO: 5.

The sequence of proteins usable in the above construct would also preferably present an identity (as indicated by the Needleman and Wunsch algorithm) equal or above 70%, preferably, equal or above 80% more preferably equal or above 90%, more preferably equal or above 92%, more preferably equal or above 93%, more preferably equal or above 94%, more preferably equal or above 95%, more preferably equal or above 96%, more preferably equal or above 97%, more preferably equal or above 98%, more preferably equal or above 99% more preferably equal or above 99.5%, more preferably equal or above 99.8% with SEQ ID NO: 6.

The sequence of proteins usable in the above construct would also preferably present an identity (as indicated by the Needleman and Wunsch algorithm) equal or above 70%, preferably, equal or above 80% more preferably equal or above 90%, more preferably equal or above 92%, more preferably equal or above 93%, more preferably equal or above 94%, more preferably equal or above 95%, more preferably equal or above 96%, more preferably equal or above 97%, more preferably equal or above 98%, more preferably equal or above 99% more preferably equal or above 99.5%, more preferably equal or above 99.8% with SEQ ID NO: 7.

The sequence of proteins usable in the above construct would preferably present an identity (as indicated by the Needleman and Wunsch algorithm) equal or above 70%, preferably, equal or above 80% more preferably equal or above 90%, more preferably equal or above 92%, more preferably equal or above 93%, more preferably equal or above 94%, more preferably equal or above 95%, more preferably equal or above 96%, more preferably equal or above 97%, more preferably equal or above 98%, more preferably equal or above 99% more preferably equal or above 99.5%, more preferably equal or above 99.8% with SEQ ID NO: 8.

Using these similar sequences to produce transgenic plants makes it possible to obtain an equivalent technical effect as the one presented in the present application: increase of yield for these transgenic plants (as compared with isogenic plants not carrying the transgene), in particular in stressed conditions, and specifically in nitrogen stress conditions.

The invention also encompasses a vector containing the nucleic acid construct (expression cassette) of the invention.

A vector, such as a plasmid, can thus be used for transforming host cells. The construction of vectors for transformation of host cells is within the capability of one skilled in the art following standard techniques.

The decision as to whether to use a vector for transforming a cell, or which vector to use, is guided by the method of transformation selected, and by the host cell selected.

Where a naked nucleic acid introduction method is used, then the vector can be the minimal nucleic acid sequences necessary to confer the desired phenotype, without the need for additional sequences.

Possible vectors include the Ti plasmid vectors, shuttle vectors designed merely to maximally yield high numbers of copies, episomal vectors containing minimal sequences necessary for ultimate replication once transformation has occurred, transposon vectors, including the possibility of RNA forms of the gene sequences. The selection of vectors and methods to construct them are commonly known to persons of ordinary skill in the art and are described in general technical references (Mullis, K B (1987), Methods in Enzymology).

For other transformation methods requiring a vector, selection of an appropriate vector is relatively simple, as the constraints are minimal. The apparent minimal traits of the vector are that the desired nucleic acid sequence be introduced in a relatively intact state. Thus, any vector which produces a plant carrying the introduced DNA sequence should be sufficient. Also, any vector which introduces a substantially intact RNA which can ultimately be converted into a stably maintained DNA sequence should be acceptable.

For transformation methods within a plant cell, one can cite methods of direct transfer of genes such as direct micro-injection into plant embryos, vacuum infiltration or electroporation, direct precipitation by means of PEG or the bombardment by gun of particles covered with the plasmidic DNA of interest.

It is preferred to transform the plant cell with a bacterial strain, in particular *Agrobacterium*, in particular *Agrobacterium tumefaciens*. In particular, it is possible to use the method described by Ishida et al. (Nature Biotechnology, 14, 745-750, 1996) for the transformation of monocotyledons.

However, any additional attached vector sequences which confer resistance to degradation of the nucleic acid fragment to be introduced, which assists in the process of genomic integration or provides a means to easily select for those cells or plants which are actually, in fact, transformed are advantageous and greatly decrease the difficulty of selecting useable transgenic plants.

The vector can exist, for example, in the form of a phage, a plasmid or a cosmid. The construction of such expression vectors for transformation is well known in the art and uses standard techniques. Mention may be made of the methods described by Sambrook et al. (1989).

For transforming bacteria, a vector is generally defined as being a nucleic acid molecule that possesses elements that allows it to be maintained within said host cell (such as an origin of replication that works in this bacterial host cell).

The invention also encompasses a host cell containing the nucleic acid construct (expression cassette) as described above.

The decision as to whether to use a given host cell, or which host cell to use, is guided by the method of transformation.

The host cell can be any prokaryotic or eukaryotic cell. Any of a large number of available and well-known host cells may be used in the practice of this invention. The selection of a particular host is dependent upon a number of factors recognized by the art. These include, for example, compatibility with the chosen expression vector, bio-safety and costs. Useful hosts include bacteria such as *E. coli* sp. or *Agrobacterium*. A plant host cell, may be also used, notably an angiosperm plant cell, monocotyledon as dicotyledon plant cell, particularly a cereal or oily plant cell, selected in particular from the group consisting of maize, wheat, barley, rice, rape and sunflower, preferentially maize. Another preferred plant is wheat. Another preferred plant is rice. Another preferred plant is barley.

More particularly, the host cell used in carrying out the invention is *Agrobacterium tumefaciens*, according to the method described in the article of An et al., 1986, or *Agrobacterium rhizogenes*, according to the method described in the article of Jouanin et al., 1987.

In a specific embodiment, said expression cassette is stably integrated within the genome of said host cell. This embodiment is particularly interesting for plant host cells. Stable integration within the genome means that the expression cassette can be transmitted to the progeny of said host cell upon division.

The invention also encompasses a plant containing at least one cell containing the expression cassette as defined above, preferably stably integrated within its genome.

A part of a transgenic plant, in particular fruit, seed, grain or pollen, comprising such a cell or generated from such a cell is also encompassed by the invention.

It is reminded that a whole plant can be regenerated from a single transformed plant cell. Thus, in a further aspect the present invention provides transgenic plants (or parts of them) including the expression cassette as described above. The regeneration can be performed by known methods.

The seeds which grow by fertilization from this plant, also contain this transgene in their genome.

Said plant or part of a plant according to the invention can be a plant or a part of it from various species, notably an Angiosperm, Monocotyledons as Dicotyledons.

It is preferably a cereal or oily plant. As used herein, the term "oily plant" denotes a plant that is capable of producing oil, and preferably that is cultivated for oil production.

Said plant is preferably selected from the group consisting of maize, rice, wheat, barley, rape and sunflower. In a preferred embodiment, said plant is maize. In another preferred embodiment, said plant is wheat.

The invention thus relates in particular to a transgenic maize or a transgenic wheat, containing at least one cell comprising, stably integrated in its genome, the expression cassette as disclosed above.

In a specific embodiment, said plant, in particular said maize, comprises multiple cells containing, stably integrated in their genome, the expression cassette as described above. In this embodiment, it is possible that some cells of said plant do not contain the transgene.

Due to the use of a root promoter, expression of the MYB related protein is thus predominant in the roots. This may be observed by performing Northern blot on RNA obtained from different organs of the plant, and detecting an expression at least ten times higher in the roots than in other organs.

In a specific embodiment, said transgene (comprising the expression cassette as disclosed) is present in all cells of said plant, in particular said maize or wheat.

In another embodiment, the transgene is introduced within the plant cells such as being expressed transiently, or through a genetic construct not integrated in the genome. Thus, agro-infiltration or any other methods, such as injection or spray, are contemplated for transient expression.

Hybrid plants obtained by crossing plants according to the invention also form part of the invention, when they contain at least one cell containing the expression cassette of the invention.

Any plant as described above can contain one or more transgenes in addition to the cassette according to the invention. One may mention transgenes conferring male sterility, male fertility, resistance to a herbicide (notably glyphosate, glufosinate, imidazolinone, sulfonylurea, L-phosphinotricine, triazine, benzonitrile), resistance to insects (notably a transgene coding for a *Bacillus thuringiensis* toxin), tolerance to water stress. These plants can be obtained by crossing said plants of the invention with other plants containing said transgenes. Alternatively, plants can be co-transformed with an expression cassette containing several different transgenes, including the transgene of the invention.

As demonstrated in the examples, said transgenic plants comprising an expression cassette according to the invention present an increased yield as compared to control plants corresponding to non-transgenic plants not comprising said expression cassette.

Said generated plant shall present an increased yield, in normal or stressed conditions, as compared to an isogenic plant that does not contain said expression cassette in its genome, and/or shall be able to maintain the yield observed in normal conditions when grown in stressed conditions.

As disclosed above, the stress may be any biotic or abiotic stress, but is preferably a nitrogen stress, in particular a stress as described in the examples.

In this method, it is clear that the measure of yield is checked by sowing and harvesting of a multiplicity of plants that contain the transgene, the yield of which is then compared with the yield obtained with a second group of plants not containing said transgene, and grown under the same culture conditions (sowing and harvest at the same time, on comparable parcels, use of the same amount of fertilizers, water . . . ).

It is also clear that comparison is to be performed on a second group of plants that is isogenic to the plants having the transgene. As indicated above, these "isogenic" plants differs from the plants harboring the transgene at very few loci (less than 20, more preferably less than 10), in addition to not carry said transgene. In particular a plant carrying the transgene isogenic to another plant of interest may be obtained by at least four backcrosses in the isogenic plant of interest, followed by at least one self-fertilization. Preferably, the isogenic plants are homozygous lines.

Said increased yield may be observed in normal conditions or in stress conditions. In the present invention nitrogen stress (in particular as disclosed in the examples) is a stress for which the transgenic plants of the invention would present maintained or increased yield with regards to isogenic plants.

Increased yield in stress conditions (or stress tolerance) can be measured by the ability of the transgenic plant to maintain yield under stress conditions compared to normal conditions (which is considered to be achieved when the yield observed in stressed conditions is at least 90%, 94%, 95%, 96%, 97%, 98%, 99% or 100% of the yield obtained for the same plant in non-stressed (normal) conditions). It can also be measured by the ability of the transgenic plant to increase yield under stress conditions compared to control plants grown under stress conditions (at least 101%, 102%, 103%, 104%, 105%, 106%, 107%, 108%, 109%, 110%, 111%, 112%, 113%, 114%, or even 115%).

As intended herein, stress conditions comprise specific conditions that are applied to a plant at a specific development stage such as that they induce a yield decrease of at least 8%, 10%, preferentially at least 15% and more preferentially at least 20% between the control plants in normal and in stress conditions. As a matter of illustration, one can cite heat stress conditions that may be applied during the flowering stage (in particular for wheat) or hydric stress before the flowering stage or after the fertilization, (in particular during the grain filling stage for maize).

Consequently, the invention also relates to various methods of making or using the plants of the invention.

Therefore, the invention also relates to a method for obtaining a transgenic plant containing at least one cell comprising a transgene comprising the nucleic acid construct as described above, comprising the steps consisting of:

a) transforming at least a plant cell or plant tissue with a vector containing the nucleic acid construct according to the invention;

b) cultivating the cell(s) or plant tissue thus transformed so as to generate a transgenic plant containing at least a cell which contains, in its genome, at least the nucleic acid construct as disclosed above.

In particular, the invention encompasses a method for increasing yield in a plant, comprising the steps consisting of:

a) transforming at least a plant cell or plant tissue with a vector containing, as a transgene, a nucleic acid construct comprising:
   i. a promoter active in roots (as disclosed above), operatively linked to
   ii. a nucleic acid coding for a MYB related protein;
b) cultivating the cell(s) or plant tissue thus transformed so as to generate a transgenic plant containing at least a cell which contains, in its genome, at least said nucleic acid construct.

wherein said plant presents a increased yield than a plant isogenic but for said nucleic acid construct.

The nucleic acid construct is as disclosed above.

One can also cite a method for obtaining a plant containing a transgene, wherein said transgene comprises the nucleic acid construct as disclosed above, comprising the steps of a) performing the method as described above (transformation of plant cells and regeneration) in order to obtain a transgenic plant, wherein said transgene comprises said nucleic acid construct described above, b) crossing said transgenic plant with a plant line which does not contain said transgene (the receiver plant line)

c) selecting, among the progeny, plants that contain said transgene and that have a good genome ratio with regard to said receiver plant line, d) back-crossing said selected plants with said receiver plant line e) repeating steps c) and d) if necessary until a line isogenic with said receiving line (and containing said transgene) is obtained, f) optionally, performing self-fertilization in order to obtain a plant homozygotic for said transgene.

The selection of step c) is preferably performed, by genotyping using molecular markers (for example microsatellite markers), making it possible to define the contribution of each of the two parents to the progeny. One would thus select, in the progeny, plants carrying the transgene and having more markers from the receiver plant line than from the parent containing the transgene.

Plants (in particular maize or wheat) which possess the transgene, may also be selected from the progeny, in a conventional manner by molecular biology methods (such as PCR or Southern blotting).

Said generated plant can also be used in a selection (breeding) process for obtaining a plant with improved yield.

The invention thus also relates to a method for producing a plant that can be used in a selection (breeding) process or scheme for obtaining a plant with improved yield, comprising the step of transforming a plant cell with a vector according to the invention, and regenerating a transgenic plant which comprises at least one cell which contain the transgene comprising the expression cassette as described above.

The introgression of the transgene in a given plant is in particular carried out by selection, according to methods known in the art (crossing and self-pollination). The plants are in particular selected using molecular markers.

The principle is recalled below:

A series of back crosses are performed between the elite line (in which one wishes to introduce the determinant) and a line that already carries said determinant (the donor line). During the back crosses, one can select individuals carrying the determinant and having recombed the smallest fragment from the donor line around the determinant. Specifically, by virtue of molecular markers, the individuals having, for the markers closest to the determinant, the genotype of the elite line are selected.

In addition, it is also possible to accelerate the return to the elite parent by virtue of the molecular markers distributed over the entire genome. At each back cross, the individuals having the most fragments derived from the recurrent elite parent will be chosen.

Selection is important as it is often preferable to sow and harvest plant lines that have been optimized, in particular for the location in which they are cultured. Consequently, one needs to introduce the transgene in said adapted lines having otherwise agronomic quality characteristics.

The invention also relates to a method for growing a plant, comprising the step of sowing a plant seed, wherein said plant seed contains the nucleic acid construct as described above, and growing plants from this sowed seed.

The invention also relates to a method for increasing plant yield under normal conditions, comprising the step of sowing plant seeds, wherein said plant seeds contain the expression cassette of the invention and growing plants from these sowed seeds, and wherein the yield obtained from said grown plants is increased as compared to the yield obtained from isogenic plants grown from seeds which do not contain said expression cassette The invention also relates to a method for increasing or maintaining plant yield under stressed conditions, comprising the step of sowing plant seeds, wherein said plant seeds contain the nucleic acid construct as described above, and growing plants from these sowed seeds, wherein at least part of the growing phase is made under stress conditions, and wherein the yield obtained from said grown plants is increased as compared to the yield obtained from plants grown from seeds which do not contain said nucleic acid construct or the yield obtained from said grown plants is maintained as compared to the yield obtained from plants containing said nucleic acid construct and grown in normal conditions.

The invention also relates to a method of growing plants, comprising the step of sowing seeds containing the nucleic acid construct as described above, and growing plants from the sowed seeds.

The invention may also comprise the step of harvesting said plants.

The invention also relates to a method for harvesting plants comprising the step of harvesting plants of the invention.

In particular, in the methods as described above, a hydric stress is applied to the plants during their growth.

A method for selecting (i.e. screening, identifying) a plant that can be used in a selection (breeding) process for obtaining a plant with improved yield, which comprises the step of selecting, in a population of plants, the plants containing the expression cassette as described above, is also part of the invention.

A breeding process for obtaining a plant with improved yield is performed as follows: the yield of a plurality of plants gives the reference yield level which is to be improved. The plant with improved yield is obtained, when the yield observed after sowing and harvesting said plant is higher than the yield of reference. Said plant with improved yield is obtained by known methods in the art, by crossing, back-crossing and stabilizing plants which present a yield In a specific embodiment, the selection is performed through the use of a marker that is specific to the transgene. In this embodiment, the selection step is thus preferably preceded by a step comprising genotyping said population of cereals.

In a specific embodiment, the selection step is preceded by a step comprising extracting the RNA from the individuals in said population.

In a specific embodiment, the selection step is preceded by a step comprising extracting proteins from the individuals in said population.

In a specific embodiment, said population is the progeny obtained from crossing a transgenic plant, wherein said transgene comprises the expression cassette as described above, with a plant line which does not contain said transgene (the receiver plant line).

A method for identifying a plant with improved yield, which comprises the step of identifying, in a population of plants, the plants containing the expression cassette as described above, is also part of the invention. Improved yield is determined after comparison with a isogenic plant which does not contain the expression cassette.

In a specific embodiment, the identification is performed through the use of a marker that is specific to the transgene. In this embodiment, the identification step is thus preferably preceded by a step comprising genotyping said population of cereals.

In a specific embodiment, the identification step is preceded by a step comprising extracting the RNA from the individuals in said population.

In a specific embodiment, the identification step is preceded by a step comprising extracting proteins from the individuals in said population.

In a specific embodiment, said population is the progeny obtained from crossing a transgenic plant, wherein said transgene comprises the expression cassette as described above, with a plant line which does not contain said transgene (the receiver plant line).

The invention also relates to a method for obtaining a hybrid plant, wherein said hybrid plant contains the expression cassette as described above stably integrated within its genome. Said method comprises the step of crossing a first homozygous line, which contains said expression cassette stably integrated within its genome, with a second homozygous line.

This plant can be homozygous (if each homozygous parent has the expression cassette as described above stably integrated within its genome) or heterozygous for the transgene present on said expression cassette.

In a preferred embodiment, the methods are applied to a cereal (in particular, rice, maize, wheat, barley). It is preferred when said plant is maize or wheat.

DESCRIPTION OF THE FIGURES

FIG. 3 represents the results obtained for different events bearing the MYB related coding sequence operably linked to either a constitutive (Actin promoter+actin intron) or root specific promoter. Promoter: promoter used; Location type: ND: Nitrogen Deficiency; Normal: no Nitrogen Deficiency; Phenotype: phenotype observed for the tested events: Yield after moisture normalization, or moisture. The results (yield and moisture) are presented as percentages of the results observed for the controls.

FIG. 4 represents the alignment of the MYB domains of sequences 2 to 8.

EXAMPLE 1—EXPERIMENTAL VALIDATION OF TMMYB GENE FUNCTION IN NITROGEN DEFICIENCY CONDITIONS IN WHEAT

Materials & Methods

Wheat leaf samples were collected on 2 sites (La Miniére and Boigneville stations—Arvalis Institut du Végétal; France): one for cultivar Arche grown in field, and samples were harvested for cultivar Soissons grown in greenhouse.

Different nitrogen treatments were applied to lead to samples with a range of Nitrogen Nutrional Index (NNI) from 0.39 to 1.58. During wheat culture, sampling was done at different stages.

Total RNAs were extracted from all the samples with the SV96 Total RNA Isolation System (Promega) according to the manufacturer recommendations. RNA integrity was verified on the Agilent Bioanalyzer and presence of potential genomic DNA was checked by QPCR on RNA. In the absence of genomic DNA no amplification is expected from RNA.

For each sample 2 μg of total RNA were reverse transcribed using the High capacity reverse transcription kit (Applied Biosystems) and random primers in 100 μl. RT reaction was then 1/10th diluted and 2 μl of cDNA used for the amplification. Each RNA sample was submitted to 2 independent RT reactions for technical reproducibility evaluation.

Quantitative PCR was performed on a AB17900 machine (Applied Biosystems), using Applied Biosystems reagents. The PCR reactions consisted of a hot-start Taq Polymerase activation step of 95° C. for 5 minutes, followed by 2 steps amplification cycles (denaturation 95°, 30 sec, annealing/elongation 60°, 1 min).

Expression levels of mRNA for the *Triticum monoccocum* MYB (TmMYB) gene were calculated using the Ct estimated by the SDS software (Applied Biosystems) and normalized across samples using 4 control genes. Relative expression was then considered as the ΔCt between TmMYB gene and the average of controls.

Results

In order to validate the role of the TmMYB gene in Nitrogen Deficiency conditions an experiment on two bread wheat genotypes, Arche and Soissons, was conducted on leaf collected at different stages under different nitrogen constraints. The N nutrition index (NNI) value was calculated for each sample.

Figure 1:
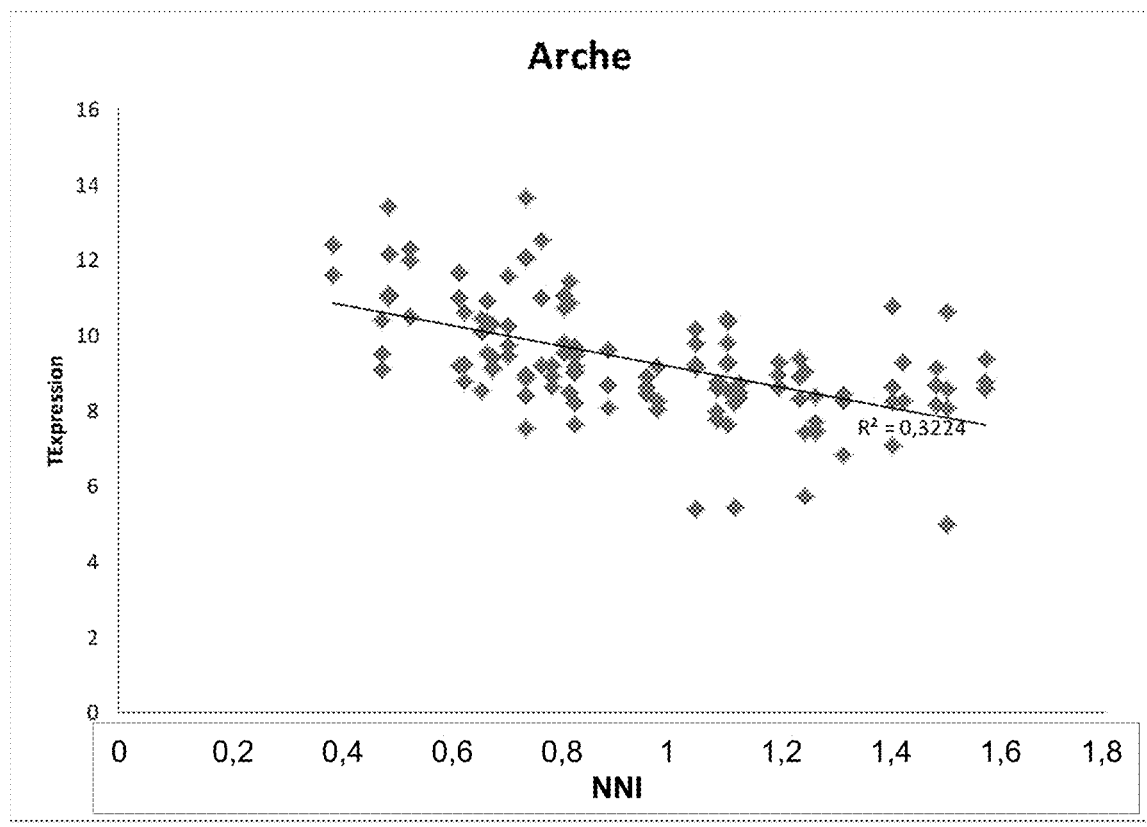
FIG. 1 represents the level of expression (ΔΔCT) for TmMYB gene, as a function of the Nitrogen Nutrional Index (NNI) on Arche genotypes.
Figure 2:
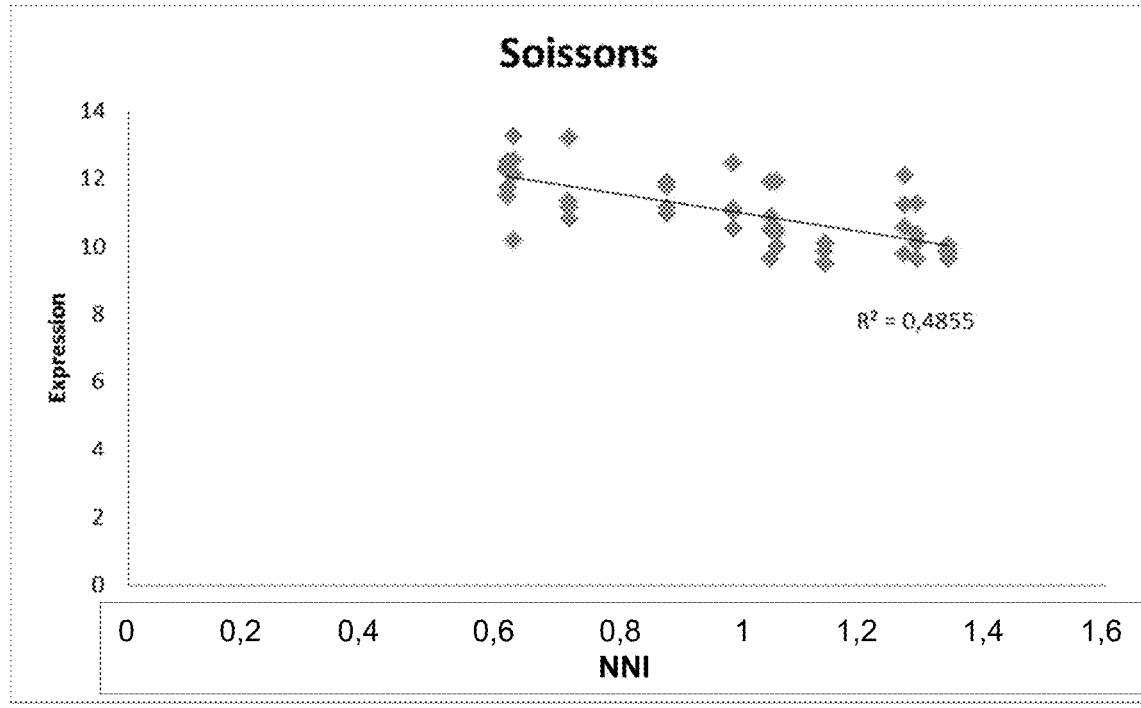
FIG. 2 represents the level of expression (ΔΔCT) for TmMYB gene, as a function of the Nitrogen Nutrional Index (NNI) for leaf samples on Soissons genotypes

Moreover, for the same samples, RNA was extracted and the expression pattern of TmMYB was analysed through qPCR using sequence specific primers (forward: TTTTCTCCCCCTGCCGAC (SEQ ID NO: 25); reverse: GTCATACCGTTCGTCGTCCA (SEQ ID NO: 26)). The results are shown in FIGS. 1 and 2.

A significant correlation of $R^2=0.32$ and 0.49 was found between the expression (ΔΔCT values) of the TmMYB gene and the NNI score of the samples for both the Arche and Soissons genotypes, respectively. These results confirm that the TmMYB gene is a candidate gene for increasing yield under Nitrogen Deficiency conditions.

EXAMPLE 2: CLONING OF TMMYB DOWNSTREAM A ROOT AND CONSTITUVE PROMOTER AND TRANSFORMATION

TmMYB sequence (depicted as SEQ ID NO:1 (cDNA) and SEQ ID NO:2 (protein)) was cloned via a GATEWAY LR reaction, between the constitutive *Oryza sativa* Actin promoter (proOsActin, SEQ ID NO: 16) (McElroy et al. 1990) with the *Oryza sativa* Actin intron (intOsActin, exemplified in SEQ ID NO: 17) (McElroy et al. 1990), and a 3' *Arabidospis thaliana* Nopaline synthase (Nos) termination sequence (tAtNos, depicted in SEQ ID NO: 18) (Depicker et al. 1982), into the destination binary plasmid pSC4Act-R1R2-SCV forming pBIOS1776.

The binary vector pSC4Act-R1R2-SCV is a derivative of the binary vector pSCV nos nptII which is a derivative of pSCV1 (Firek et al. 1993) which contains a nos promoter driving a Kanamycin resistance gene, cloned between the EcoRV and EcoRI sites of pSCV1.

The TmMYB sequence was cloned via a GATEWAY LR reaction, between *Avaena strigosa* Sad1 promoter (SEQ ID NO: 19, Haralampidis et al. 2001 and Qi et al, 2006) and a *Arabidopsis thaliana* Sac66 termination sequence (terAtSac66, depicted in SEQ ID NO:15)(Jenkins et al. 1999)). In the same way, constructs were made using promoters proZmTIP2_3, proOsRCG2 and proHvIDS2 with the TmMYB sequence as depicted by SEQ ID NO: 20 to SEQ ID NO: 22 respectively. The *Otyza sativa* RCC3 promoter was also used (pro0110) (SEQ ID NO: 13, $1^{st}$ sequence of WO 2004/070039) and completed with the *Zea mays* shunkren intron (intSh1, exemplified in SEQ ID NO: 14) (Werr et al. 1985), and terAtSac66 (SEQ ID NO: 15) and led to the construct depicted as SEQ ID NO:23. All constructs were cloned into a destination binary plasmid pBIOS-type.

The binary vector pBIOS is a derivative of the binary vector pSCV nos nptII which is a derivative of pSCV1 (Firek et al. 1993) which contains a nos promoter driving a Kanamycin resistance gene, cloned between the EcoRV and EcoRI sites of pSCV1.

The binary plasmids were transferred into agrobacteria EHA105 according to Komari et al. (1996). Maize and wheat were transformed Wheat cultivar (NB01) was transformed with these agrobacterial strains essentially as described by WO 2000/063398. Wheat transgenic events were generated for each construct described above.

EXAMPLE 3: WHEAT FIELD TRIALS

Field trials show that seed yield and nitrogen yield efficiency under both optimal and nitrogen deficient conditions are improved when MYB is overexpressed.

1) Field Trials:

Homozygous transgenic lines were self-pollinized for seed increase.

T4 (root promoter-intshr-TmMYB-terSac66) homozygous plants were used for field trials.

Controls are obtained by bulking null segregant siblings isolated from T1 segregation. The null segregants are used as a reference for statistical analysis. They thus differ from the tested lines at very few loci, and for the presence of the transgene. These controls are thus quasi-isogenic to the tested lines. Improved yield was observed for wheat plants containing the TmMYB construct as compared to the controls, as can be seen in FIG. 3.

Field evaluation was performed under two Nitrogen conditions:

In normal (optimal) growing condition with an optimal Nitrogen fertilization. The applied Nitrogen rate was calculated using local guideline.

In nitrogen stress condition, the applied Nitrogen rate was between 0 and 50% of the optimal Nitrogen rate.

After harvest, the Nitrogen stress condition was eventually verified and characterized when a statistically significant seed yield loss (i.e. generally a seed loss between 5% and 30%) is observed, as compared to the seed yield observed under the normal condition.

Yield was calculated as follows:

During harvest, grain weight and grain moisture are measured using on-board equipment on the combine harvester.

Grain weight is then normalized to moisture at 15%, using the following formula:

Normalized grain weight=measured grain weight×
(100−measured moisture(as a percentage))/85
(which is 100−normalized moisture at 15%)

As an example, if the measured grain moisture is 25%, the normalized grain weight will be: normalized grain weight=measured grain weight×75/85.

Yield is then expressed in a conventional unit (such as quintal per hectare).

2) Experimental Design:

Field trials were conducted in 2013 (2 N stress locations) and 2014 (1 N stress location, 1 N stress and yield (normal) location, 1 yield (normal) location)

In 2013, plants were sown between April 23 (location 1) and May 11th (location 2).

In 2014, plants were sown between April 16 and May 17th.

The experimental design was randomized complete block or Lattice with 4 replicate seeded at 360 seeds/m$^2$.

A bulk of null segregant of the construct was used as control in these experiments. 4 transgenic events of the construct T01822 were used for the field trials in 4 replicates.

Results are represented in FIG. 3 with the yield expressed in percentage compared to the control.

In nitrogen deficiency (ND) conditions, in 2013 the observed yield ranged from 100.7% to 108% of the mean of the yield of the controls with a global average of 104.35%. No effect on seed moisture content was observed.

In nitrogen deficiency (ND) conditions, in 2014 the observed yield ranged from 102.6% to 105.1% of the mean of the yield of the controls with a global average of 103.85%. No effect on seed moisture content was observed.

In standard condition, in 2014 the yield observed ranged from 103.6% to 106.5% of the mean of the yield of the controls with a global average of 105.5%. No effect on seed moisture content was observed.

This figure demonstrates that the transgenic plants expressing TmMYB protein under a root promoter present an increased yield stability (normalized for moisture) in normal and ND conditions. No other phenotypes were observed for these plants.

Decrease of yield is observed when the TmMYB protein is expressed under a constitutive promoter. In standard condition, in 2014 the yield observed ranged from 91.5% to 97% of the mean of the yield of the controls with a global average of 94.4%. The seed moisture content is observed with a global average of 96.6%.

The invention claimed is:

1. A nucleic acid construct comprising: a promoter functional in a plant root, which is operably linked to a nucleic acid molecule comprising a nucleic acid sequence encoding a Myb-related transcription factor protein, wherein said MYB-related transcription factor protein comprises an amino acid sequence having at least 99% amino acid sequence identity to the amino acid sequence as set forth in SEQ ID NO: 2, and wherein said promoter is heterologous to said nucleic acid molecule.

2. The nucleic acid construct of claim 1, wherein the Myb-related transcription factor protein is as set forth in SEQ ID NO: 2.

3. The nucleic acid construct of claim 1, wherein said promoter is selected from the group consisting of SEQ ID NO: 9, SEQ ID NO: 10, SEQ ID NO: 11, SEQ ID NO: 12, SEQ ID NO: 13 and SEQ ID NO: 19.

4. A host cell comprising the nucleic acid construct of claim 1.

5. The host cell of claim 4, wherein said nucleic acid construct is stably integrated within the genome of said host cell.

6. A transgenic plant, or a part of a transgenic plant part thereof transformed with the nucleic acid construct of claim 1.

7. The transgenic plant or part of the transgenic plant of claim 6, which is a cereal plant.

8. The transgenic plant or part of the transgenic plant of claim 7, wherein said cereal plant is selected from the group consisting of maize, wheat, barley, and rice.

9. A method for increasing plant yield, comprising sowing transgenic plant seeds, wherein said transgenic plant seeds are transformed with the nucleic acid construct of claim 1 and growing transgenic plants from said transgenic sowed plant seeds, wherein said Myb-related transcription factor protein is overexpressed in said grown transgenic plants, and wherein the yield obtained from said grown transgenic plants is increased as compared to control plants of the same plant species which do not contain the nucleic acid construct and are grown under identical conditions.

10. A method for increasing plant yield under nitrogen deficiency conditions, comprising sowing transgenic plant seeds, wherein said transgenic plant seeds are transformed with the nucleic acid construct of claim 1 and growing transgenic plants from the transgenic plant sowed seeds under nitrogen deficiency conditions, wherein said Myb-related transcription factor protein is overexpressed in said grown transgenic plants, and wherein the yield of said grown transgenic plants is increased as compared to control plants of the same species which do not contain the nucleic acid construct and are grown under said nitrogen deficiency conditions.

11. The nucleic acid construct of claim 2, wherein said promoter is selected from the group consisting of SEQ ID NO: 9, SEQ ID NO: 10, SEQ ID NO: 11, SEQ ID NO: 12, SEQ ID NO: 13 and SEQ ID NO: 19.

12. A host cell comprising the nucleic acid construct of claim 11.

13. The nucleic acid construct of claim 1, wherein said Myb-related transcription factor protein comprises an amino acid sequence having at least 99.5% amino acid sequence identity to the amino acid sequence as set forth in SEQ ID NO: 2.

14. The nucleic acid construct of claim 1, wherein said promoter is a root-specific promoter.

* * * * *